United States Patent
Aumer et al.

(10) Patent No.: US 10,945,618 B2
(45) Date of Patent: Mar. 16, 2021

(54) PHYSIOLOGICAL MONITORING DEVICES AND METHODS FOR NOISE REDUCTION IN PHYSIOLOGICAL SIGNALS BASED ON SUBJECT ACTIVITY TYPE

(71) Applicant: Valencell, Inc., Raleigh, NC (US)

(72) Inventors: Michael Edward Aumer, Raleigh, NC (US); Steven Francis LeBoeuf, Raleigh, NC (US)

(73) Assignee: Valencell, Inc., Raleigh, NC (US)

( * ) Notice: Subject to any disclaimer, the term of this patent is extended or adjusted under 35 U.S.C. 154(b) by 112 days.

(21) Appl. No.: 15/922,610

(22) Filed: Mar. 15, 2018

(65) Prior Publication Data
US 2018/0199837 A1      Jul. 19, 2018

Related U.S. Application Data

(63) Continuation of application No. 15/299,684, filed on Oct. 21, 2016, now Pat. No. 10,610,158.
(Continued)

(51) Int. Cl.
*A61B 5/024* (2006.01)
*A61B 5/11* (2006.01)
(Continued)

(52) U.S. Cl.
CPC ........ *A61B 5/02427* (2013.01); *A61B 5/1118* (2013.01); *A61B 5/721* (2013.01);
(Continued)

(58) Field of Classification Search
CPC ...... A61B 5/721; A61B 5/1118; A61B 5/1455
See application file for complete search history.

(56) References Cited

U.S. PATENT DOCUMENTS

| | | |
|---|---|---|
| 3,595,219 A | 7/1971 | Friedlander et al. |
| 4,240,882 A | 12/1980 | Ang et al. |

(Continued)

FOREIGN PATENT DOCUMENTS

| | | |
|---|---|---|
| AU | 2015101130 | 10/2015 |
| CN | 101212927 | 7/2008 |

(Continued)

OTHER PUBLICATIONS

Asada et al. "Mobile Monitoring with Wearable Photoplethysmographic Biosensors" IEEE Engineering in Medicine and Biology Magazine (pp. 28-40) (May/Jun. 2003).
(Continued)

*Primary Examiner* — Gary Jackson
*Assistant Examiner* — Zahed Kabir
(74) *Attorney, Agent, or Firm* — Myers Bigel, P.A.

(57) ABSTRACT

Methods and apparatus for monitoring a subject are described. A monitoring device configured to be attached to a body of a subject includes a sensor that is configured to detect and/or measure physiological information from the subject and at least one motion sensor configured to detect and/or measure subject motion information. The physiological sensor and motion sensor are in communication with a processor that is configured to receive and analyze signals produced by the physiological sensor and motion sensor. The processor is configured to process motion sensor signals to identify an activity characteristic of the subject. Once an activity characteristic is identified, the processor is configured to select a noise reference in response to identification of the activity characteristic of the subject, and then process physiological sensor signals using the noise reference to generate an output signal having reduced noise relative to the physiological sensor signal, to produce physiological information about the subject.

22 Claims, 11 Drawing Sheets

Related U.S. Application Data

(60) Provisional application No. 62/475,746, filed on Mar. 23, 2017, provisional application No. 62/245,919, filed on Oct. 23, 2015.

(51) Int. Cl.
*A61B 5/00* (2006.01)
*A61B 5/08* (2006.01)
*A61B 5/0456* (2006.01)
*A61B 5/1455* (2006.01)
*A61B 5/0205* (2006.01)
*A61B 5/021* (2006.01)

(52) U.S. Cl.
CPC ............ *A61B 5/0022* (2013.01); *A61B 5/021* (2013.01); *A61B 5/0205* (2013.01); *A61B 5/02055* (2013.01); *A61B 5/02405* (2013.01); *A61B 5/02438* (2013.01); *A61B 5/0456* (2013.01); *A61B 5/0816* (2013.01); *A61B 5/1455* (2013.01); *A61B 5/6815* (2013.01); *A61B 5/6831* (2013.01); *A61B 5/7253* (2013.01); *A61B 2560/0242* (2013.01); *A61B 2562/0219* (2013.01)

(56) References Cited

U.S. PATENT DOCUMENTS

| | | |
|---|---|---|
| 4,281,645 A | 8/1981 | Jobsis |
| 4,331,154 A | 5/1982 | Broadwater et al. |
| 4,371,406 A | 2/1983 | Li |
| 4,438,772 A | 3/1984 | Slavin |
| 4,491,760 A | 1/1985 | Linvill |
| 4,521,499 A | 6/1985 | Switzer |
| 4,541,905 A | 9/1985 | Kuwana et al. |
| 4,586,513 A | 5/1986 | Hamaguri |
| 4,592,807 A | 6/1986 | Switzer |
| 4,655,225 A | 4/1987 | Dahne et al. |
| 4,830,014 A | 5/1989 | Goodman et al. |
| 4,882,492 A | 11/1989 | Schlager |
| 4,896,676 A | 1/1990 | Sasaki |
| 4,928,704 A | 5/1990 | Hardt |
| 4,952,890 A | 8/1990 | Swanson |
| 4,952,928 A | 8/1990 | Carroll et al. |
| 4,957,109 A | 9/1990 | Groeger et al. |
| 5,002,060 A | 3/1991 | Nedivi |
| 5,022,970 A | 6/1991 | Cook et al. |
| 5,025,791 A | 6/1991 | Niwa |
| 5,079,421 A | 1/1992 | Knudson et al. |
| 5,080,098 A | 1/1992 | Willett et al. |
| 5,086,229 A | 2/1992 | Rosenthal et al. |
| 5,139,025 A | 8/1992 | Lewis et al. |
| 5,143,078 A | 9/1992 | Mather et al. |
| 5,226,417 A | 7/1993 | Swedlow et al. |
| 5,237,994 A | 8/1993 | Goldberger |
| 5,299,570 A | 4/1994 | Hatschek |
| 5,348,002 A | 9/1994 | Caro |
| 5,377,100 A | 12/1994 | Pope et al. |
| 5,386,819 A | 2/1995 | Kaneko et al. |
| 5,431,170 A | 7/1995 | Mathews |
| 5,448,082 A | 9/1995 | Kim |
| 5,482,036 A | 1/1996 | Diab et al. |
| 5,492,129 A | 2/1996 | Greenberger |
| 5,494,043 A | 2/1996 | O'Sullivan et al. |
| 5,499,301 A | 3/1996 | Sudo et al. |
| 5,581,648 A | 12/1996 | Sahagen |
| 5,596,987 A | 1/1997 | Chance |
| 5,662,117 A | 9/1997 | Bittman |
| 5,673,692 A | 10/1997 | Schulze et al. |
| 5,697,374 A | 12/1997 | Odagiri et al. |
| 5,711,308 A | 1/1998 | Singer |
| 5,725,480 A | 3/1998 | Oosta et al. |
| 5,743,260 A | 4/1998 | Chung et al. |
| 5,779,631 A | 7/1998 | Chance |
| 5,797,841 A | 8/1998 | Delonzor et al. |
| 5,807,114 A | 9/1998 | Hodges et al. |
| 5,807,267 A | 9/1998 | Bryars et al. |
| 5,817,008 A | 10/1998 | Rafert et al. |
| 5,820,560 A | 10/1998 | Sinderby et al. |
| 5,846,190 A | 12/1998 | Woehrle |
| 5,853,005 A | 12/1998 | Scanlon |
| 5,904,654 A | 5/1999 | Wohltmann et al. |
| 5,938,593 A | 8/1999 | Ouellette |
| 5,954,644 A | 9/1999 | Dettling et al. |
| 5,964,701 A | 10/1999 | Asada et al. |
| 5,971,931 A | 10/1999 | Raff |
| 5,974,338 A | 10/1999 | Asano et al. |
| 5,995,858 A | 11/1999 | Kinast |
| 6,004,274 A | 12/1999 | Nolan et al. |
| 6,006,119 A | 12/1999 | Soller et al. |
| 6,013,007 A | 1/2000 | Root et al. |
| 6,022,748 A | 2/2000 | Charych et al. |
| 6,023,541 A | 2/2000 | Merchant et al. |
| 6,030,342 A | 2/2000 | Amano et al. |
| 6,045,511 A | 4/2000 | Ott et al. |
| 6,067,006 A | 5/2000 | O'Brien |
| 6,070,093 A | 5/2000 | Oosta et al. |
| 6,078,829 A | 6/2000 | Uchida et al. |
| 6,080,110 A | 6/2000 | Thorgersen |
| 6,081,742 A | 6/2000 | Amano et al. |
| 6,122,042 A | 9/2000 | Wunderman et al. |
| 6,148,229 A | 11/2000 | Morris, Sr. et al. |
| 6,155,983 A | 12/2000 | Kosuda et al. |
| 6,168,567 B1 | 1/2001 | Pickering et al. |
| 6,186,145 B1 | 2/2001 | Brown |
| 6,198,394 B1 | 3/2001 | Jacobsen et al. |
| 6,198,951 B1 | 3/2001 | Kosuda et al. |
| 6,205,354 B1 | 3/2001 | Gellermann et al. |
| 6,231,519 B1 | 5/2001 | Blants et al. |
| 6,267,721 B1 | 7/2001 | Welles |
| 6,283,915 B1 | 9/2001 | Aceti et al. |
| 6,285,816 B1 | 9/2001 | Anderson et al. |
| 6,289,230 B1 | 9/2001 | Chaiken et al. |
| 6,298,314 B1 | 10/2001 | Blackadar et al. |
| 6,332,868 B1 | 12/2001 | Sato et al. |
| 6,358,216 B1 | 3/2002 | Kraus et al. |
| 6,361,660 B1 | 3/2002 | Goldstein |
| 6,371,925 B1 | 4/2002 | Imai et al. |
| 6,374,129 B1 | 4/2002 | Chin et al. |
| 6,415,167 B1 | 7/2002 | Blank et al. |
| 6,443,890 B1 | 9/2002 | Schulze et al. |
| 6,444,474 B1 | 9/2002 | Thomas et al. |
| 6,454,718 B1 | 9/2002 | Clift |
| 6,458,080 B1 | 10/2002 | Brown et al. |
| 6,470,893 B1 | 10/2002 | Boesen |
| 6,513,532 B2 | 2/2003 | Mault et al. |
| 6,514,278 B1 | 2/2003 | Hibst et al. |
| 6,527,711 B1 | 3/2003 | Stivoric et al. |
| 6,527,712 B1 | 3/2003 | Brown et al. |
| 6,529,754 B2 | 3/2003 | Kondo |
| 6,534,012 B1 | 3/2003 | Hazen et al. |
| 6,556,852 B1 | 4/2003 | Schulze et al. |
| 6,569,094 B2 | 5/2003 | Suzuki et al. |
| 6,571,117 B1 | 5/2003 | Marbach |
| 6,605,038 B1 | 8/2003 | Teller et al. |
| 6,608,562 B1 | 8/2003 | Kimura et al. |
| 6,616,613 B1 | 9/2003 | Goodman |
| 6,631,196 B1 | 10/2003 | Taenzer et al. |
| 6,647,378 B2 | 11/2003 | Kindo |
| 6,656,116 B2 | 12/2003 | Kim et al. |
| 6,694,180 B1 | 2/2004 | Boesen |
| 6,702,752 B2 | 3/2004 | Dekker |
| 6,725,072 B2 | 4/2004 | Steuer et al. |
| 6,745,061 B1 | 6/2004 | Hicks et al. |
| 6,748,254 B2 | 6/2004 | O'Neil et al. |
| 6,760,610 B2 | 7/2004 | Tschupp et al. |
| 6,783,501 B2 | 8/2004 | Takahashi et al. |
| 6,808,473 B2 | 10/2004 | Hisano et al. |
| 6,859,658 B1 | 2/2005 | Krug |
| 6,893,396 B2 | 5/2005 | Schulze et al. |
| 6,941,239 B2 | 9/2005 | Unuma et al. |
| 6,953,435 B2 | 10/2005 | Kondo et al. |
| 6,954,644 B2 | 10/2005 | Johansson et al. |
| 6,996,427 B2 | 2/2006 | Ali et al. |

(56) References Cited

U.S. PATENT DOCUMENTS

| | | |
|---|---|---|
| 6,997,879 B1 | 2/2006 | Turcott |
| 7,018,338 B2 | 3/2006 | Vetter et al. |
| 7,024,369 B1 | 4/2006 | Brown et al. |
| 7,030,359 B2 | 4/2006 | Romhild |
| 7,034,694 B2 | 4/2006 | Yamaguchi et al. |
| 7,039,454 B1 | 5/2006 | Kaga et al. |
| 7,041,062 B2 | 5/2006 | Friedrichs et al. |
| 7,043,287 B1 | 5/2006 | Khalil et al. |
| 7,048,687 B1 | 5/2006 | Reuss et al. |
| 7,054,674 B2 | 5/2006 | Cane et al. |
| 7,088,234 B2 | 8/2006 | Naito et al. |
| 7,107,088 B2 | 9/2006 | Aceti |
| 7,113,815 B2 | 9/2006 | O'Neil et al. |
| 7,117,032 B2 | 10/2006 | Childre et al. |
| 7,144,375 B2 | 12/2006 | Kosuda |
| 7,163,512 B1 | 1/2007 | Childre et al. |
| 7,175,601 B2 | 2/2007 | Verjus et al. |
| 7,190,986 B1 | 3/2007 | Hannula et al. |
| 7,209,775 B2 | 4/2007 | Bae et al. |
| 7,217,224 B2 | 5/2007 | Thomas |
| 7,252,639 B2 | 8/2007 | Kimura et al. |
| 7,263,396 B2 | 8/2007 | Chen et al. |
| 7,289,837 B2 | 10/2007 | Mannheimer et al. |
| 7,336,982 B2 | 2/2008 | Yoo |
| 7,341,559 B2 | 3/2008 | Schulz et al. |
| 7,376,451 B2 | 5/2008 | Mahony et al. |
| 7,378,954 B2 | 5/2008 | Wendt |
| 7,470,234 B1 | 12/2008 | Elhag et al. |
| 7,483,730 B2 | 1/2009 | Diab et al. |
| 7,486,988 B2 | 2/2009 | Goodall et al. |
| 7,507,207 B2 | 3/2009 | Sakai et al. |
| 7,519,327 B2 | 4/2009 | White |
| 7,526,327 B2 | 4/2009 | Blondeau et al. |
| 7,583,994 B2 | 9/2009 | Scholz |
| 7,620,450 B2 | 11/2009 | Kim et al. |
| 7,625,285 B2 | 12/2009 | Breving |
| 7,652,569 B2 | 1/2010 | Kiff et al. |
| 7,689,437 B1 | 3/2010 | Teller et al. |
| 7,695,440 B2 | 4/2010 | Kondo et al. |
| 7,725,147 B2 | 5/2010 | Li et al. |
| 7,756,559 B2 | 7/2010 | Abreu |
| 7,843,325 B2 | 11/2010 | Otto |
| 7,894,869 B2 | 2/2011 | Hoarau |
| 7,914,468 B2 | 3/2011 | Shalon et al. |
| 7,991,448 B2 | 8/2011 | Edgar, Jr. et al. |
| 7,998,079 B2 | 8/2011 | Nagai et al. |
| 8,050,728 B2 | 11/2011 | Al-Ali et al. |
| 8,055,319 B2 | 11/2011 | Oh et al. |
| 8,055,330 B2 | 11/2011 | Egozi |
| 8,059,924 B1 | 11/2011 | Letant et al. |
| 8,130,105 B2 | 3/2012 | Al-Ali et al. |
| 8,137,270 B2 | 3/2012 | Keenan et al. |
| 8,157,730 B2 | 4/2012 | Leboeuf et al. |
| 8,172,459 B2 | 5/2012 | Abreu |
| 8,175,670 B2 | 5/2012 | Baker, Jr. et al. |
| 8,204,730 B2 | 6/2012 | Liu et al. |
| 8,204,786 B2 | 6/2012 | Leboeuf et al. |
| 8,233,955 B2 | 7/2012 | Al-Ali et al. |
| 8,251,903 B2 | 8/2012 | Leboeuf et al. |
| 8,255,027 B2 | 8/2012 | Al-Ali et al. |
| 8,255,029 B2 | 8/2012 | Addison et al. |
| 8,303,512 B2 | 11/2012 | Kosuda et al. |
| 8,320,982 B2 | 11/2012 | Leboeuf et al. |
| 8,323,982 B2 | 12/2012 | Leboeuf et al. |
| 8,328,420 B2 | 12/2012 | Abreu |
| 8,416,959 B2 | 4/2013 | Lott et al. |
| 8,491,492 B2 | 7/2013 | Shinar et al. |
| 8,504,679 B2 | 8/2013 | Spire et al. |
| 8,506,524 B2 | 8/2013 | Graskov et al. |
| 8,512,242 B2 | 8/2013 | Leboeuf et al. |
| 8,647,270 B2 | 2/2014 | Leboeuf et al. |
| 8,652,040 B2 | 2/2014 | Leboeuf et al. |
| 8,652,409 B2 | 2/2014 | Leboeuf et al. |
| 8,679,008 B2 | 3/2014 | Hughes et al. |
| 8,700,111 B2 | 4/2014 | Leboeuf et al. |
| 8,702,607 B2 | 4/2014 | Leboeuf et al. |
| 8,730,048 B2 | 5/2014 | Shen et al. |
| 8,788,002 B2 | 7/2014 | Leboeuf et al. |
| 8,886,269 B2 | 11/2014 | Leboeuf et al. |
| 8,888,701 B2 | 11/2014 | Leboeuf et al. |
| 8,923,941 B2 | 12/2014 | Leboeuf et al. |
| 8,929,965 B2 | 1/2015 | Leboeuf et al. |
| 8,929,966 B2 | 1/2015 | Leboeuf et al. |
| 8,934,952 B2 | 1/2015 | Leboeuf et al. |
| 8,942,776 B2 | 1/2015 | Leboeuf et al. |
| 8,961,415 B2 | 2/2015 | Leboeuf et al. |
| 8,996,332 B2 | 3/2015 | Kahn |
| 9,005,129 B2 | 4/2015 | Venkatraman et al. |
| 9,044,180 B2 | 6/2015 | Leboeuf et al. |
| 9,289,175 B2 | 3/2016 | Leboeuf et al. |
| 9,801,552 B2 | 10/2017 | Romesburg |
| 9,808,204 B2 | 11/2017 | Leboeuf et al. |
| 9,943,266 B2 | 4/2018 | Adams et al. |
| 2001/0015123 A1 | 8/2001 | Nishitani et al. |
| 2001/0044588 A1 | 11/2001 | Mault |
| 2001/0049471 A1 | 12/2001 | Suzuki et al. |
| 2002/0035340 A1 | 3/2002 | Fraden et al. |
| 2002/0143242 A1 | 10/2002 | Nemirovski |
| 2002/0156386 A1 | 10/2002 | Dardik et al. |
| 2002/0156654 A1 | 10/2002 | Roe et al. |
| 2002/0173780 A1 | 11/2002 | Altshuler et al. |
| 2002/0186137 A1 | 12/2002 | Skardon |
| 2002/0188210 A1 | 12/2002 | Aizawa |
| 2002/0194002 A1 | 12/2002 | Petrushin |
| 2003/0002705 A1 | 1/2003 | Boesen |
| 2003/0007631 A1 | 1/2003 | Bolognesi et al. |
| 2003/0045785 A1 | 3/2003 | Diab et al. |
| 2003/0050563 A1 | 3/2003 | Suribhotla et al. |
| 2003/0064712 A1 | 4/2003 | Gaston et al. |
| 2003/0065257 A1 | 4/2003 | Mault et al. |
| 2003/0083583 A1 | 5/2003 | Kovtun et al. |
| 2003/0109030 A1 | 6/2003 | Uchida et al. |
| 2003/0130586 A1 | 7/2003 | Starobin et al. |
| 2003/0181795 A1 | 9/2003 | Suzuki et al. |
| 2003/0181798 A1 | 9/2003 | Al-Ali |
| 2003/0181817 A1 | 9/2003 | Mori |
| 2003/0212336 A1 | 11/2003 | Lee et al. |
| 2003/0220584 A1 | 11/2003 | Honeyager et al. |
| 2003/0222268 A1 | 12/2003 | Yocom et al. |
| 2004/0004547 A1 | 1/2004 | Appelt et al. |
| 2004/0022700 A1 | 2/2004 | Kim et al. |
| 2004/0030581 A1 | 2/2004 | Leven |
| 2004/0034289 A1 | 2/2004 | Teller et al. |
| 2004/0034293 A1 | 2/2004 | Kimball |
| 2004/0039254 A1 | 2/2004 | Stivoric et al. |
| 2004/0073455 A1 | 4/2004 | McConnochie et al. |
| 2004/0075677 A1 | 4/2004 | Loyall et al. |
| 2004/0077934 A1 | 4/2004 | Massad |
| 2004/0081621 A1 | 4/2004 | Arndt et al. |
| 2004/0082842 A1 | 4/2004 | Lumba et al. |
| 2004/0097796 A1 | 5/2004 | Berman et al. |
| 2004/0103146 A1 | 5/2004 | Park |
| 2004/0117204 A1 | 6/2004 | Mazar et al. |
| 2004/0120844 A1 | 6/2004 | Tribelsky et al. |
| 2004/0122294 A1 | 6/2004 | Hatlestad et al. |
| 2004/0122702 A1 | 6/2004 | Sabol et al. |
| 2004/0133123 A1 | 7/2004 | Leonhardt et al. |
| 2004/0135571 A1 | 7/2004 | Uutela et al. |
| 2004/0138578 A1 | 7/2004 | Pineda et al. |
| 2004/0158167 A1 | 8/2004 | Smith et al. |
| 2004/0186387 A1 | 9/2004 | Kosuda et al. |
| 2004/0186390 A1 | 9/2004 | Ross et al. |
| 2004/0219056 A1 | 11/2004 | Tribelsky et al. |
| 2004/0220488 A1 | 11/2004 | Vyshedskiy et al. |
| 2004/0228494 A1 | 11/2004 | Smith |
| 2004/0242976 A1 | 12/2004 | Abreu |
| 2004/0254501 A1 | 12/2004 | Mault |
| 2005/0004458 A1 | 1/2005 | Kanayama et al. |
| 2005/0007582 A1 | 1/2005 | Villers et al. |
| 2005/0021519 A1 | 1/2005 | Ghouri |
| 2005/0027216 A1 | 2/2005 | Guillemaud et al. |
| 2005/0030540 A1 | 2/2005 | Thornton |
| 2005/0033200 A1 | 2/2005 | Soehren et al. |
| 2005/0036212 A1 | 2/2005 | Saito |

(56) References Cited

U.S. PATENT DOCUMENTS

| | | |
|---|---|---|
| 2005/0038349 A1 | 2/2005 | Choi et al. |
| 2005/0043630 A1 | 2/2005 | Buchert |
| 2005/0059870 A1 | 3/2005 | Aceti |
| 2005/0070809 A1 | 3/2005 | Acres |
| 2005/0084666 A1 | 4/2005 | Pong et al. |
| 2005/0100866 A1 | 5/2005 | Arnone et al. |
| 2005/0101845 A1 | 5/2005 | Nihtila |
| 2005/0101872 A1 | 5/2005 | Sattler et al. |
| 2005/0113167 A1 | 5/2005 | Buchner et al. |
| 2005/0113656 A1 | 5/2005 | Chance |
| 2005/0113703 A1 | 5/2005 | Farringdon et al. |
| 2005/0116820 A1 | 6/2005 | Goldreich |
| 2005/0119833 A1 | 6/2005 | Nanikashvili |
| 2005/0148883 A1 | 7/2005 | Boesen |
| 2005/0154264 A1 | 7/2005 | Lecompte et al. |
| 2005/0177034 A1 | 8/2005 | Beaumont |
| 2005/0187448 A1 | 8/2005 | Petersen et al. |
| 2005/0187453 A1 | 8/2005 | Petersen et al. |
| 2005/0192515 A1 | 9/2005 | Givens et al. |
| 2005/0196009 A1 | 9/2005 | Boesen |
| 2005/0203349 A1 | 9/2005 | Nanikashvili |
| 2005/0203357 A1 | 9/2005 | Debreczeny et al. |
| 2005/0209516 A1 | 9/2005 | Fraden |
| 2005/0212405 A1 | 9/2005 | Negley |
| 2005/0222487 A1 | 10/2005 | Miller, III et al. |
| 2005/0222903 A1 | 10/2005 | Buchheit et al. |
| 2005/0228244 A1 | 10/2005 | Banet |
| 2005/0228299 A1 | 10/2005 | Banet |
| 2005/0228463 A1 | 10/2005 | Mac et al. |
| 2005/0245839 A1 | 11/2005 | Stivoric et al. |
| 2005/0258816 A1 | 11/2005 | Zen et al. |
| 2005/0259811 A1 | 11/2005 | Kimm et al. |
| 2006/0009685 A1 | 1/2006 | Finarov et al. |
| 2006/0012567 A1 | 1/2006 | Sicklinger |
| 2006/0063993 A1 | 3/2006 | Yu et al. |
| 2006/0074333 A1 | 4/2006 | Huiku |
| 2006/0084878 A1 | 4/2006 | Banet et al. |
| 2006/0084879 A1 | 4/2006 | Nazarian et al. |
| 2006/0122520 A1 | 6/2006 | Banet et al. |
| 2006/0123885 A1 | 6/2006 | Yates et al. |
| 2006/0140425 A1 | 6/2006 | Berg et al. |
| 2006/0142665 A1 | 6/2006 | Garay et al. |
| 2006/0202816 A1 | 9/2006 | Crump et al. |
| 2006/0205083 A1 | 9/2006 | Zhao |
| 2006/0210058 A1 | 9/2006 | Kock et al. |
| 2006/0211922 A1 | 9/2006 | Al-Ali et al. |
| 2006/0211924 A1 | 9/2006 | Dalke et al. |
| 2006/0217598 A1 | 9/2006 | Miyajima et al. |
| 2006/0224059 A1 | 10/2006 | Swedlow et al. |
| 2006/0240558 A1 | 10/2006 | Zhao |
| 2006/0246342 A1 | 11/2006 | MacPhee |
| 2006/0251277 A1 | 11/2006 | Cho |
| 2006/0251334 A1 | 11/2006 | Oba et al. |
| 2006/0252999 A1 | 11/2006 | Devaul et al. |
| 2006/0258927 A1* | 11/2006 | Edgar, Jr. ........... A61B 5/14551 600/336 |
| 2006/0264730 A1 | 11/2006 | Stivoric et al. |
| 2006/0287590 A1 | 12/2006 | McEowen |
| 2006/0292533 A1 | 12/2006 | Selod |
| 2006/0293921 A1 | 12/2006 | McCarthy et al. |
| 2007/0004449 A1 | 1/2007 | Sham |
| 2007/0004969 A1 | 1/2007 | Kong et al. |
| 2007/0015992 A1 | 1/2007 | Filkins et al. |
| 2007/0021206 A1 | 1/2007 | Sunnen |
| 2007/0027367 A1 | 2/2007 | Oliver et al. |
| 2007/0027399 A1 | 2/2007 | Chou |
| 2007/0036383 A1 | 2/2007 | Romero |
| 2007/0050215 A1 | 3/2007 | Kil et al. |
| 2007/0060800 A1 | 3/2007 | Drinan et al. |
| 2007/0060819 A1 | 3/2007 | Altshuler et al. |
| 2007/0063850 A1 | 3/2007 | Devaul et al. |
| 2007/0082789 A1 | 4/2007 | Nissila et al. |
| 2007/0083092 A1 | 4/2007 | Rippo et al. |
| 2007/0083095 A1 | 4/2007 | Rippo et al. |
| 2007/0088221 A1 | 4/2007 | Stahmann |
| 2007/0093702 A1 | 4/2007 | Yu et al. |
| 2007/0106167 A1 | 5/2007 | Kinast |
| 2007/0112273 A1 | 5/2007 | Rogers |
| 2007/0112598 A1 | 5/2007 | Heckerman et al. |
| 2007/0116314 A1 | 5/2007 | Grilliot et al. |
| 2007/0118043 A1 | 5/2007 | Oliver et al. |
| 2007/0135717 A1 | 6/2007 | Uenishi et al. |
| 2007/0165872 A1 | 7/2007 | Bridger et al. |
| 2007/0167850 A1 | 7/2007 | Russell et al. |
| 2007/0191718 A1 | 8/2007 | Nakamura |
| 2007/0197878 A1 | 8/2007 | Shklarski |
| 2007/0197881 A1 | 8/2007 | Wolf et al. |
| 2007/0213020 A1 | 9/2007 | Novac |
| 2007/0230714 A1 | 10/2007 | Armstrong |
| 2007/0233403 A1 | 10/2007 | Alwan et al. |
| 2007/0265097 A1 | 11/2007 | Havukainen |
| 2007/0270667 A1 | 11/2007 | Coppi et al. |
| 2007/0270671 A1 | 11/2007 | Gal |
| 2007/0293781 A1 | 12/2007 | Sims et al. |
| 2007/0299330 A1 | 12/2007 | Couronne et al. |
| 2008/0001735 A1 | 1/2008 | Tran |
| 2008/0004536 A1 | 1/2008 | Baxi et al. |
| 2008/0015424 A1 | 1/2008 | Bernreuter |
| 2008/0039731 A1 | 2/2008 | McCombie et al. |
| 2008/0076972 A1 | 3/2008 | Dorogusker et al. |
| 2008/0081963 A1 | 4/2008 | Naghavi et al. |
| 2008/0081972 A1 | 4/2008 | Debreczeny |
| 2008/0086533 A1 | 4/2008 | Neuhauser et al. |
| 2008/0096726 A1 | 4/2008 | Riley et al. |
| 2008/0114220 A1 | 5/2008 | Banet et al. |
| 2008/0132798 A1 | 6/2008 | Hong et al. |
| 2008/0133699 A1 | 6/2008 | Craw et al. |
| 2008/0141301 A1 | 6/2008 | Azzaro et al. |
| 2008/0154098 A1 | 6/2008 | Morris et al. |
| 2008/0154105 A1 | 6/2008 | Lemay |
| 2008/0165017 A1 | 7/2008 | Schwartz |
| 2008/0170600 A1 | 7/2008 | Sattler et al. |
| 2008/0171945 A1 | 7/2008 | Dotter |
| 2008/0177162 A1 | 7/2008 | Bae et al. |
| 2008/0200774 A1 | 8/2008 | Luo |
| 2008/0203144 A1 | 8/2008 | Kim |
| 2008/0221414 A1 | 9/2008 | Baker, Jr. |
| 2008/0221461 A1 | 9/2008 | Zhou et al. |
| 2008/0249594 A1 | 10/2008 | Dietrich et al. |
| 2008/0287752 A1 | 11/2008 | Stroetz et al. |
| 2008/0312517 A1 | 12/2008 | Genoe et al. |
| 2009/0005662 A1 | 1/2009 | Petersen et al. |
| 2009/0006457 A1 | 1/2009 | Stivoric et al. |
| 2009/0010461 A1 | 1/2009 | Klinghult et al. |
| 2009/0010556 A1 | 1/2009 | Uchibayashi et al. |
| 2009/0030350 A1 | 1/2009 | Yang et al. |
| 2009/0054751 A1 | 2/2009 | Babashan et al. |
| 2009/0054752 A1 | 2/2009 | Jonnalagadda et al. |
| 2009/0069645 A1 | 3/2009 | Nielsen et al. |
| 2009/0082994 A1 | 3/2009 | Schuler et al. |
| 2009/0088611 A1 | 4/2009 | Buschmann |
| 2009/0093687 A1 | 4/2009 | Telfort et al. |
| 2009/0105548 A1 | 4/2009 | Bart |
| 2009/0105556 A1 | 4/2009 | Fricke et al. |
| 2009/0112101 A1 | 4/2009 | Furness, III et al. |
| 2009/0131761 A1 | 5/2009 | Moroney, III et al. |
| 2009/0131764 A1 | 5/2009 | Lee et al. |
| 2009/0175456 A1 | 7/2009 | Johnson |
| 2009/0177097 A1 | 7/2009 | Ma et al. |
| 2009/0214060 A1 | 8/2009 | Chuang et al. |
| 2009/0221888 A1 | 9/2009 | Wijesiriwardana |
| 2009/0227853 A1 | 9/2009 | Wijesiriwardana |
| 2009/0240125 A1 | 9/2009 | Such et al. |
| 2009/0253992 A1 | 10/2009 | Van Der Loo |
| 2009/0253996 A1 | 10/2009 | Lee et al. |
| 2009/0264711 A1 | 10/2009 | Schuler et al. |
| 2009/0270698 A1 | 10/2009 | Shioi et al. |
| 2009/0281435 A1 | 11/2009 | Ahmed et al. |
| 2009/0287067 A1 | 11/2009 | Dorogusker et al. |
| 2009/0299215 A1 | 12/2009 | Zhang |
| 2010/0004517 A1 | 1/2010 | Bryenton et al. |
| 2010/0022861 A1 | 1/2010 | Cinbis et al. |
| 2010/0045663 A1 | 2/2010 | Chen et al. |
| 2010/0100013 A1 | 4/2010 | Hu et al. |

(56) References Cited

U.S. PATENT DOCUMENTS

| | | |
|---|---|---|
| 2010/0113948 A1 | 5/2010 | Yang et al. |
| 2010/0168531 A1 | 7/2010 | Shaltis et al. |
| 2010/0172522 A1 | 7/2010 | Mooring et al. |
| 2010/0179389 A1 | 7/2010 | Moroney, III et al. |
| 2010/0185105 A1 | 7/2010 | Baldinger |
| 2010/0217100 A1 | 8/2010 | Leboeuf et al. |
| 2010/0217102 A1 | 8/2010 | Leboeuf et al. |
| 2010/0217103 A1 | 8/2010 | Abdul-Hafiz et al. |
| 2010/0222655 A1 | 9/2010 | Starr et al. |
| 2010/0228315 A1 | 9/2010 | Nielsen |
| 2010/0234714 A1 | 9/2010 | Mercier et al. |
| 2010/0268056 A1 | 10/2010 | Picard et al. |
| 2010/0274100 A1 | 10/2010 | Behar et al. |
| 2010/0274109 A1 | 10/2010 | Hu et al. |
| 2010/0292589 A1 | 11/2010 | Goodman |
| 2010/0298653 A1 | 11/2010 | McCombie et al. |
| 2011/0028810 A1 | 2/2011 | Van Slyke et al. |
| 2011/0028813 A1 | 2/2011 | Watson et al. |
| 2011/0066007 A1 | 3/2011 | Banet et al. |
| 2011/0081037 A1 | 4/2011 | Oh et al. |
| 2011/0098112 A1 | 4/2011 | Leboeuf et al. |
| 2011/0105869 A1 | 5/2011 | Wilson et al. |
| 2011/0112382 A1 | 5/2011 | Li et al. |
| 2011/0130638 A1 | 6/2011 | Raridan |
| 2011/0142371 A1 | 6/2011 | King et al. |
| 2011/0178564 A1 | 7/2011 | Keefe |
| 2011/0288379 A1 | 11/2011 | Wu |
| 2012/0030547 A1 | 2/2012 | Raptis et al. |
| 2012/0095303 A1 | 4/2012 | He |
| 2012/0150052 A1 | 6/2012 | Buchheim et al. |
| 2012/0156933 A1 | 6/2012 | Kreger et al. |
| 2012/0172702 A1 | 7/2012 | Koyrakh et al. |
| 2012/0179011 A1 | 7/2012 | Moon et al. |
| 2012/0190948 A1 | 7/2012 | Vetter et al. |
| 2012/0203081 A1 | 8/2012 | Leboeuf et al. |
| 2012/0226111 A1 | 9/2012 | Leboeuf et al. |
| 2012/0226112 A1 | 9/2012 | Leboeuf et al. |
| 2012/0277548 A1 | 11/2012 | Burton |
| 2013/0053661 A1 | 2/2013 | Alberth et al. |
| 2013/0072765 A1 | 3/2013 | Kahn et al. |
| 2013/0197377 A1 | 8/2013 | Kishi et al. |
| 2013/0245387 A1 | 9/2013 | Patel |
| 2013/0336495 A1 | 12/2013 | Burgett et al. |
| 2014/0012105 A1 | 1/2014 | Leboeuf et al. |
| 2014/0051940 A1 | 2/2014 | Messerschmidt |
| 2014/0051948 A1 | 2/2014 | Leboeuf et al. |
| 2014/0052567 A1 | 2/2014 | Bhardwaj et al. |
| 2014/0058220 A1 | 2/2014 | Leboeuf et al. |
| 2014/0073486 A1 | 3/2014 | Ahmed et al. |
| 2014/0088433 A1 | 3/2014 | Shan |
| 2014/0094663 A1 | 4/2014 | Leboeuf et al. |
| 2014/0100432 A1 | 4/2014 | Golda et al. |
| 2014/0127996 A1 | 5/2014 | Park et al. |
| 2014/0128690 A1 | 5/2014 | Leboeuf |
| 2014/0135596 A1 | 5/2014 | Leboeuf et al. |
| 2014/0140567 A1 | 5/2014 | Leboeuf et al. |
| 2014/0171755 A1 | 6/2014 | Leboeuf et al. |
| 2014/0213863 A1 | 7/2014 | Loseu et al. |
| 2014/0219467 A1 | 8/2014 | Kurtz |
| 2014/0228649 A1* | 8/2014 | Rayner ............... A61B 5/1118 600/301 |
| 2014/0235967 A1 | 8/2014 | Leboeuf et al. |
| 2014/0235968 A1 | 8/2014 | Leboeuf et al. |
| 2014/0236531 A1 | 8/2014 | Carter |
| 2014/0243617 A1 | 8/2014 | Leboeuf et al. |
| 2014/0243620 A1 | 8/2014 | Leboeuf et al. |
| 2014/0275852 A1 | 9/2014 | Hong et al. |
| 2014/0275854 A1 | 9/2014 | Venkatraman et al. |
| 2014/0275855 A1 | 9/2014 | Leboeuf et al. |
| 2014/0276119 A1* | 9/2014 | Venkatraman ........ A61B 5/721 600/479 |
| 2014/0287833 A1 | 9/2014 | Leboeuf et al. |
| 2014/0288392 A1 | 9/2014 | Hong et al. |
| 2014/0288396 A1 | 9/2014 | Leboeuf et al. |
| 2014/0288436 A1 | 9/2014 | Venkatraman et al. |
| 2014/0323829 A1 | 10/2014 | Leboeuf et al. |
| 2014/0323830 A1 | 10/2014 | Leboeuf et al. |
| 2014/0323880 A1 | 10/2014 | Ahmed et al. |
| 2014/0327515 A1 | 11/2014 | Luna et al. |
| 2014/0378844 A1 | 12/2014 | Fei |
| 2015/0011898 A1 | 1/2015 | Romesburg |
| 2015/0018636 A1* | 1/2015 | Romesburg ......... A61B 5/6817 600/301 |
| 2015/0025393 A1 | 1/2015 | Hong et al. |
| 2015/0031967 A1 | 1/2015 | Leboeuf et al. |
| 2015/0032009 A1 | 1/2015 | Leboeuf et al. |
| 2015/0057967 A1 | 2/2015 | Albinali |
| 2015/0080741 A1* | 3/2015 | LeBoeuf ............. A61B 5/6816 600/476 |
| 2015/0080746 A1* | 3/2015 | Bleich ................... G16H 20/30 600/479 |
| 2015/0157269 A1 | 6/2015 | Lisogurski et al. |
| 2015/0190085 A1 | 7/2015 | Nathan et al. |
| 2015/0196256 A1 | 7/2015 | Venkatraman et al. |
| 2015/0250396 A1 | 9/2015 | Ahmed et al. |
| 2015/0265217 A1 | 9/2015 | Penders et al. |
| 2015/0282768 A1 | 10/2015 | Luna et al. |
| 2015/0289820 A1 | 10/2015 | Miller et al. |
| 2015/0305682 A1 | 10/2015 | Leboeuf et al. |
| 2015/0342481 A1 | 12/2015 | Liu et al. |
| 2015/0366509 A1 | 12/2015 | Romesburg |
| 2016/0022220 A1 | 1/2016 | Lee et al. |
| 2016/0029964 A1 | 2/2016 | Leboeuf et al. |
| 2016/0038045 A1 | 2/2016 | Shapiro |
| 2016/0051157 A1 | 2/2016 | Waydo |
| 2016/0089033 A1 | 3/2016 | Saponas et al. |
| 2016/0089086 A1 | 3/2016 | Lin et al. |
| 2016/0094899 A1 | 3/2016 | Aumer et al. |
| 2016/0120476 A1 | 5/2016 | Liu et al. |
| 2016/0206247 A1* | 7/2016 | Morland ............. A61B 5/7207 |
| 2016/0287108 A1 | 10/2016 | Wei et al. |
| 2016/0361021 A1* | 12/2016 | Salehizadeh ........ A61B 5/0245 |
| 2017/0007166 A1 | 1/2017 | Roovers et al. |
| 2017/0034615 A1 | 2/2017 | Mankodi et al. |
| 2017/0232294 A1 | 8/2017 | Kruger et al. |
| 2017/0290549 A1 | 10/2017 | Romesburg |
| 2018/0008200 A1 | 1/2018 | Romesburg |
| 2018/0020979 A1* | 1/2018 | Wagner ................ A61B 5/0013 600/379 |
| 2018/0049645 A1 | 2/2018 | Romesburg |
| 2018/0146926 A1 | 5/2018 | Ishikawa |

FOREIGN PATENT DOCUMENTS

| | | |
|---|---|---|
| CN | 201438747 | 4/2010 |
| DE | 3910749 | 10/1990 |
| EP | 1297784 | 4/2003 |
| EP | 1480278 | 11/2004 |
| EP | 1908401 A1 | 4/2008 |
| EP | 2077091 | 7/2009 |
| EP | 2182839 | 5/2010 |
| EP | 2667769 A2 | 12/2013 |
| GB | 2408209 | 5/2005 |
| GB | 2411719 | 9/2005 |
| JP | 07241279 | 9/1995 |
| JP | 09253062 | 9/1997 |
| JP | 09299342 | 11/1997 |
| JP | 2000-116611 | 4/2000 |
| JP | 2001-025462 | 1/2001 |
| JP | 2003-159221 | 6/2003 |
| JP | 2004-513750 | 5/2004 |
| JP | 2004-283523 | 10/2004 |
| JP | 2005-040261 | 2/2005 |
| JP | 2005-270544 | 10/2005 |
| JP | 2007-044203 | 2/2007 |
| JP | 2007-185348 | 7/2007 |
| JP | 2008-136556 | 6/2008 |
| JP | 2008-279061 | 11/2008 |
| JP | 2009-153664 | 7/2009 |
| JP | 2010-526646 | 8/2010 |
| JP | 2014-068733 | 4/2014 |
| KR | 20-0204510 | 11/2000 |
| WO | 00/24064 | 4/2000 |

(56) References Cited

FOREIGN PATENT DOCUMENTS

| WO | 00/47108 | 8/2000 |
|---|---|---|
| WO | 01/08552 | 2/2001 |
| WO | 02/17782 | 3/2002 |
| WO | 2005/010568 | 2/2005 |
| WO | 2005/020121 | 3/2005 |
| WO | 2005/036212 | 4/2005 |
| WO | 2005/110238 | 11/2005 |
| WO | 2006/009830 | 1/2006 |
| WO | 2006/067690 | 6/2006 |
| WO | 2007/012931 | 2/2007 |
| WO | 2007/053146 | 5/2007 |
| WO | 2008/141306 | 11/2008 |
| WO | 2011/127063 | 10/2011 |
| WO | 2013/019494 | 2/2013 |
| WO | 2013/038296 | 3/2013 |
| WO | 2013/109389 | 7/2013 |
| WO | 2013/109390 | 7/2013 |
| WO | 2014/092932 | 6/2014 |
| WO | 2014196119 | 12/2014 |
| WO | 2015/068066 | 5/2015 |
| WO | 2015/128226 | 9/2015 |
| WO | 2015/131065 | 9/2015 |
| WO | 2017/027551 | 2/2017 |

OTHER PUBLICATIONS

BIFULCO et al. "Bluetooth Portable Device for Continuous ECG and Patient Motion Monitoring During Daily Life" Medicon 2007 IFMBE Proceedings 16:369-372 (2007).

Brodersen et al. "In-Ear Acquisition of Vital Signs Discloses New Chances for Preventive Continuous Cardiovascular Monitoring" 4th International Workshop on Wearable and Implantable Body Sensor Networks 13:189-194 (2007).

Celka et al. "Motion Resistant Earphone Located Infrared based Heart Rate Measurement Device" Proceedings of the Second Iasted International Conference on Biomedical Engineering (pp. 582-585) (Feb. 16-18, 2004).

Comtois "Implementation of Accelerometer-Based Adaptive Noise Cancellation in a Wireless Wearable Pulse Oximeter Platform for Remote Physiological Monitoring and Triage" Thesis, Worcester Polytechnic Institute (149 pages) (Aug. 31, 2007).

Comtois et al. "A Comparative Evaluation of Adaptive Noise Cancellation Algorithms for Minimizing Motion Artifacts in a Forehead-Mounted Wearable Pulse Oximeter" Proceedings of the 29th Annual International Conference of the IEEE EMBS (pp. 1528-1531) (Aug. 23-26, 2007).

Comtois et al. "A Wearable Wireless Reflectance Pulse Oximeter for Remote Triage Applications" IEEE (pp. 53-54) (2006).

Duun et al. "A Novel Ring Shaped Photodiode for Reflectance Pulse Oximetry in Wireless Applications" IEEE Sensors 2007 Conference (pp. 596-599) (2007).

Fitrainer "The Only Trainer You Need" http://itami.com©2008 FiTrainer™ (2 pages) (Downloaded Feb. 26, 2010).

Fleming et al. "A Comparison of Signal Processing Techniques for the Extraction of Breathing Rate from the Photoplethysmorgram" World Academy of Science, Engineering and Technology 30:276-280 (Oct. 2007).

Geun et al. "Measurement Site and Applied Pressure Consideration in Wrist Photoplethysmography" The 23rd International Technical Conference on Circuits/Systems, Computers and Communications (pp. 1129-1132) (2008).

Gibbs et al. "Active motion artifact cancellation for wearable health monitoring sensors using collocated MEMS accelerometers" Proc. of SPIE Smart Structures and Materials, 2005: Sensors and Smart Structures Technologies for Civil, Mechanical, and Aerospace Systems 5765:811-819 (2005).

Gibbs et al. "Reducing Motion Artifact in Wearable Bio-Sensors Using MEMS Accelerometers for Active Noise Cancellation" 2005 American Control Conference 1581-1586 (Jun. 8-10, 2005).

Haahr et al. "A Wearable "Electronic Patch" for Wireless Continuous Monitoring of Chronically Diseased Patients" Proceedings of the 5th International Workshop on Wearable and Implantable Body Sensor Networks, in conjunction with The 5th International Summer School and Symposium on Medical Devices and Biosensors (pp. 66-70) (Jun. 1-3, 2008).

Han et al. "Artifacts in wearable photoplethysmographs during daily life motions and their reduction with least mean square based active noise cancellation method" Computers in Biology and Medicine 42:387-393 (Apr. 2012).

Han et al. "Development of a wearable health monitoring device with motion artifact reduced algorithm" International Conference on Control, Automation and Systems 2007 (ICCAS 2007) (pp. 1581-1584) (Oct. 17-20, 2007).

Jiang "Motion-Artifact Resistant Design of Photoplethysmograph Ring Sensor for Driver Monitoring" Thesis, Massachusetts Institute of Technology (62 pages) (Feb. 2004).

Kuzmina et al. "Compact multi-functional skin spectrometry setup" Advanced Optical Materials, Technologies, and Devices, Proc. of SPIE 6596:65960T-1-65960T-6 (2007).

Lee et al."A Mobile Care System With Alert Mechanism" IEEE Transactions on Information Technology in Biomedicine 11(5):507-517 (Sep. 2007).

Lee et al. "Respiratory Rate Detection Algorithms by Photoplethysmography Signal Processing" 30th Annual International IEEE EMBS Conference (pp. 1140-1143) (Aug. 20-24, 2008).

Lindberg et al. "Monitoring of respiratory and heart rates using a fibre-optic sensor" Med Biol Eng Comput 30 (5):533-537 (Sep. 1992).

Luprano "Sensors and Parameter Extraction by Wearable Systems: Present Situation and Future" pHealth 2008 (29 pages) (May 21, 2008).

Lygouras et al. "Optical-Fiber Finger Photo-Plethysmograph Using Digital Techniques" IEEE Sensors Journal 2 (1):20-25 (Feb. 2002).

Maguire et al. "The Design and Clinical Use of a Reflective Brachial Photoplethysmograph" Signals and Systems Research Group, National University of Ireland (13 pages) (Apr. 2002).

Mendelson et al. "Measurement Site and Photodetector Size Considerations in Optimizing Power Consumption of a Wearable Reflectance Pulse Oximeter" Proceedings of the 25th Annual International Conference of the IEEE EMBS (pp. 3016-3019) (Sep. 17-21, 2003).

Mendelson et al. "Noninvasive Pulse Oximetry Utilizing Skin Reflectance Photoplethysmography" IEEE Transactions on Biomedical Engineering 35(10):798-805 (Oct. 1988).

Nakajima et al. "Monitoring of heart and respiratory rates by photoplethysmography using a digital filtering technique" Med. Eng. Phys. 18(5)365-372 (Jul. 1996).

Notification Concerning Transmittal of Copy of International Preliminary Report on Patentability in corresponding PCT Application No. PCT/US2016/058098 (10 pages) (dated May 3, 2018).

Poh et al. "Motion Tolerant Magnetic Earring Sensor and Wireless Earpiece for Wearable Photoplethysmography" IEEE Transactions on Information Technology in Biomedicine 14(3):786-794 (May 2010).

Renevey et al. "Wrist-Located Pulse Detection Using IR Signals, Activity and Nonlinear Artifact Cancellation" IEEE EMBS (4 pages) (2001).

Rhee et al. "Artifact-Resistant Power-Efficient Design of Finger-Ring Plethysmographic Sensors" IEEE Transactions on Biomedical Engineering 48(7):795-805 (Jul. 2001).

Shaltis "Analysis and Validation of an Artifact Resistant Design for Oxygen Saturation Measurement Using Photo Plethysmographic Ring Sensors" Thesis, Massachusetts Institute of Technology (103 pages) (Jun. 2004).

Shaw et al. "Warfighter Physiological and Environmental Monitoring: A Study for the U.S. Army Research Institute in Environmental Medicine and the Soldier Systems Center" Massachusetts Institute of Technology Lincoln Laboratory (141 pages) (Nov. 1, 2004).

Shin et al. "A Novel Headset with a Transmissive PPG Sensor for Heart Rate Measurement" 13th International Conference on Biomedical Engineering (pp. 519-522) (2009).

(56) References Cited

OTHER PUBLICATIONS

Spigulis et al. "Wearable wireless photoplethysmography sensors" Proc. of SPIE 6991:69912O-1-69912O-7 (2008).
Takatani et al. "Optical Oximetry Sensors for Whole Blood and Tissue" IEEE Engineering in Medicine and Biology (pp. 347-357) (Jun./Jul. 1994).
Vogel et al. "A System for Assessing Motion Artifacts in the Signal of a Micro-Optic In-Ear Vital Signs Sensor" 30th Annual International IEEE EMBS Conference (Aug. 20-24, 2008).
Vogel et al. "In-Ear Heart Rate Monitoring Using a Micro-Optic Reflective Sensor" Proceedings of the 29th Annual International Conference of the IEEE EMBS Cite Internationale (pp. 1375-1378) (Aug. 23-26, 2007).
Wang et al. "Multichannel Reflective PPG Earpiece Sensor With Passive Motion Cancellation" IEEE Transactions on Biomedical Circuits and Systems 1(4):235-241 (Dec. 2007).
Wang et al. "Reflective Photoplethysmograph Earpiece Sensor for Ubiquitous Heart Rate Monitoring" 4th International Workshop on Wearable and Implantable Body Sensor Networks IFMBE Proceedings 13:179-183 (2007).
Webster, John G. "Design of Pulse Oximeters" Medical Science Series, Institute of Physics Publication (143 pages) (Aug. 1997).
Wei et al. "A New Wristband Wearable Sensor Using Adaptive Reduction Filter to Reduce Motion Artifact" Proceedings of the 5th International Conference on Information Technology and Application in Biomedicine, in conjunction with The 2nd International Symposium & Summer School on Biomedical and Health Engineering (pp. 278-281) (May 30-31, 2008).
Wikipedia "Least mean squares filter" Retrieved at URL: https://en.wikipedia.org/wiki/Least_mean_squares_filter (6 pages) (Retrieved on Mar. 17, 2016).
Wood "Motion Artifact Reduction for Wearable Photoplethysmogram Sensors Using Micro Accelerometers and Laguerre Series Adaptive Filters" Thesis, Massachusetts Institute of Technology (74 pages) (Jun. 2008).
Wood et al. "Active Motion Artifact Reduction for Wearable Sensors Using Laguerre Expansion and Signal Separation" Proceedings of the 2005 IEEE Engineering in Medicine and Biology 27th Annual Conference (pp. 3571-3574) (Sep. 1-4, 2005).
Notification of Transmittal of the International Search Report and the Written Opinion of the International Searching Authority, or the Declaration, in corresponding PCT Application No. PCT/US2016/058098 (13 pages) (dated Jan. 10, 2017).
Fukushima et al. "Estimating Heart Rate using Wrist-type Photoplethysmography and Acceleration sensor while running" Conf Proc IEEE Eng Med Biol Soc. (pp. 2901-2904) (Sep. 2012).
Notification of Transmittal of the International Search Report and the Written Opinion of the International Searching Authority, or the Declaration, in corresponding PCT Application No. PCT/US2018/002621 (21 pages) (dated Jun. 18, 2018).
Extended European Search Report corresponding to European Application No. 18771241.9 (7 pages) (dated Nov. 4, 2020).

\* cited by examiner

PHYSIOLOGICAL MONITORING DEVICES AND METHODS FOR NOISE REDUCTION IN PHYSIOLOGICAL SIGNALS BASED ON SUBJECT ACTIVITY TYPE

CLAIM OF PRIORITY

This application claims priority from U.S. Provisional Patent Application No. 62/475,746 entitled "PHYSIOLOGICAL MONITORING DEVICES AND METHODS FOR NOISE REDUCTION IN PHYSIOLOGICAL SIGNALS BASED ON SUBJECT ACTIVITY TYPE" filed Mar. 23, 2017, and also claims priority as a continuation-in-part from U.S. patent application Ser. No. 15/299,684 entitled "PHYSIOLOGICAL MONITORING DEVICES AND METHODS THAT IDENTIFY SUBJECT ACTIVITY TYPE," filed Oct. 21, 2016, which claims priority from U.S. Provisional Patent Application No. 62/245,919 entitled "PHYSIOLOGICAL MONITORING DEVICES AND METHODS THAT IDENTIFY SUBJECT ACTIVITY TYPE," filed Oct. 23, 2015, in the United States Patent and Trademark Office, the disclosures of which are incorporated by reference herein in their entireties.

FIELD

The present invention relates generally to monitoring devices and methods, more particularly, to monitoring devices and methods for measuring physiological information.

BACKGROUND

Photoplethysmography (PPG) is based upon shining light into the human body and measuring how the scattered light intensity changes with each pulse of blood flow. The scattered light intensity will change in time with respect to changes in blood flow or blood opacity associated with heart beats, breaths, blood oxygen level ($SpO_2$), and the like. Such a sensing methodology may require the magnitude of light energy reaching the volume of flesh being interrogated to be steady and consistent so that small changes in the quantity of scattered photons can be attributed to varying blood flow. If the incidental and scattered photon count magnitude changes due to light coupling variation between the source or detector and the skin or other body tissue, then the signal of interest can be difficult to ascertain due to large photon count variability caused by motion artifacts. Changes in the surface area (and volume) of skin or other body tissue being impacted with photons, or varying skin surface curvature reflecting significant portions of the photons may also significantly impact optical coupling efficiency. Physical activity, such a walking, cycling, running, etc., may cause motion artifacts in the optical scatter signal from the body, and time-varying changes in photon intensity due to motion artifacts may swamp-out time-varying changes in photon intensity due to blood flow changes. Each of these changes in optical coupling can dramatically reduce the signal-to-noise ratio (S/N) of biometric PPG information to total time-varying photonic interrogation count. This can result in a much lower accuracy in metrics derived from PPG data, such as heart rate and breathing rate.

An earphone, such as a headset, earbud, etc., may be a good choice for incorporation of a photoplethysmography (PPG) device because it is a form factor that individuals are familiar with, it is a device that is commonly worn for long periods of time, and it is often used during exercise which is a time when individuals may benefit from having accurate heart rate data (or other physiological data). Unfortunately, incorporation of a photoplethysmography device into an earphone poses several challenges. For example, earphones may be uncomfortable to wear for long periods of time, particularly if they deform the ear surface. Moreover, human ear anatomy may vary significantly from person to person, so finding an earbud form that will fit comfortably in many ears may be difficult. Other form-factors for PPG devices, such as wristbands, armbands, clothing, and the like may be problematic for motion artifacts as well.

Some previous efforts to reduce motion artifacts from wearable PPG devices have focused on passive filtering, adaptive filtering (U.S. Pat. No. 8,923,941), or removing noise associated with footsteps (U.S. Pat. No. 8,157,730) with harmonics associated with a subject's cadence (US 2015/0366509). Each of these methods is associated with both strengths and weaknesses, depending on the wearable PPG sensor location or the type of motion noise that is present for the subject wearing the PPG sensor.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

According to some embodiments of the present invention, a monitoring device configured to be attached to a body of a subject includes a sensor that is configured to detect and/or measure physiological information from the subject (e.g., a PPG sensor, etc.), at least one motion sensor configured to detect and/or measure subject motion information, and at least one processor that is configured to receive and analyze physiological sensor signals produced by the physiological sensor and motion sensor signals produced by the motion sensor. The monitoring device may be configured to be positioned at or within an ear of the subject, secured to an appendage of the subject, or integrated into a form-factor that is wearable at a location of the body of the subject (for example, on a wrist). The physiological sensor may be an optical sensor that includes at least one optical emitter and at least one optical detector, although various other types of sensors may be utilized. The at least one processor is configured to process motion sensor signals to identify an activity characteristic of the subject. For example, the at least one processor is configured to determine if the subject is engaged in a periodic activity such as exercising, running, walking, etc., or if the subject is engaged in a lifestyle or non-periodic activity such as reading a book, desk work, eating, etc. A motion sensor's signal during random motion associated with lifestyle activities will be different than the signal during periodic activities. Once an activity characteristic is determined, the at least one processor is configured to select a noise reference in response to identification of the activity characteristic of the subject, and then process physiological sensor signals using the noise reference to generate output signals having reduced noise relative to the physiological sensor signals and produce physiological information about the subject.

In some embodiments, the at least one motion sensor may be first and second motion sensors, and selecting the noise reference may include selecting the first motion sensor responsive to identification of the activity characteristic as periodic motion, or selecting the second motion sensor responsive to identification of the activity characteristic as non-periodic motion.

In some embodiments, the physiological sensor may be an optical sensor, and a signal response of the second motion sensor may more closely correspond to motion-related optical noise present in the physiological sensor signal than a signal response of the first motion sensor.

In some embodiments, processing the physiological sensor signal using the noise reference may include processing the physiological sensor signal using a frequency-domain-based algorithm or circuit responsive to identification of the activity characteristic as periodic motion, or processing the physiological sensor signal using a time-domain-based algorithm or circuit responsive to identification of the activity characteristic as non-periodic motion.

In some embodiments, the physiological sensor may be a photoplethysmography (PPG) sensor, the first motion sensor may be an inertial sensor, and wherein the second motion sensor may be an optomechanical sensor.

In some embodiments, processing the physiological sensor signal using the noise reference may further include, in response to identification of the activity characteristic as periodic motion, processing the physiological sensor signal using a first algorithm or circuit, or, in response to identification of the activity characteristic as non-periodic motion, processing the physiological sensor signal using a second algorithm or circuit that is different from the first algorithm or circuit.

In some embodiments, the first algorithm or circuit may be based on frequency-domain processing and/or filtering, and wherein the second algorithm or circuit may be based on time-domain processing and/or filtering.

In some embodiments, the first and second algorithms or circuits may utilize a same sensor or sensors of the at least one motion sensor.

In some embodiments, the first algorithm or circuit may be configured to perform spectral subtraction, and the second algorithm or circuit may be configured to perform adaptive filtering.

In some embodiments, the optomechanical sensor may be configured to modulate light generated by an optical emitter in response to body motion, and to direct the light upon a pathway which is substantially unaffected by blood flow.

In some embodiments, body motion information contained in the noise reference may be greater than blood flow information contained therein.

In some embodiments, the noise reference may include information associated with motion of the subject and may be substantially free of information associated with blood flow of the subject.

In some embodiments, the physiological information may include one or more of the following: subject heart rate, subject respiration rate, subject respiratory rate interval (RRi), subject heart rate variability (HRV), subject blood pressure, subject blood analyte levels, subject cardiovascular properties.

According to some embodiments of the present invention, a monitoring device configured to be attached to a bodily location of a subject includes a physiological sensor configured to detect and/or measure physiological data from the subject and generate a physiological sensor signal representative thereof, at least one motion sensor configured to detect and/or measure subject motion data and generate a motion sensor signal representative thereof, and at least one processor coupled to the physiological sensor and the motion sensor. The at least one processor is configured to perform operations including processing the motion sensor signal received from the at least one motion sensor to identify an activity characteristic of the subject, selecting a noise reference in response to identification of the activity characteristic, and processing the physiological sensor signal received from the physiological sensor using the noise reference to generate an output signal having reduced noise relative to the physiological sensor signal.

According to some embodiments of the present invention, a computer program product includes a non-transitory computer readable storage medium having computer readable program code embodied therein. When executed by at least one processor, the computer readable program code causes the at least one processor to perform operations including processing a motion sensor signal received from at least one motion sensor to identify an activity characteristic of the subject, selecting a noise reference in response to identification of the activity characteristic, and processing a physiological sensor signal received from the physiological sensor using the noise reference to generate an output signal having reduced noise relative to the physiological sensor signal.

Monitoring devices according to embodiments of the present invention can be advantageous over some conventional monitoring devices because, by detecting an activity characteristic of a subject, a corresponding noise reference can be selected and/or modified to reduce noise that may be present in a physiological sensor signal so as to provide more accurate physiological information about a subject. For example, for optimal heart rate tracking accuracy, it may be advantageous to have some context about the type of activity being performed by a subject (i.e., whether the subject is engaged in lifestyle activities or periodic activities) to select a noise reference that may more closely correspond to motion-related noise in the signal from which the heart rate signal.

It is noted that aspects of the invention described with respect to one embodiment may be incorporated in a different embodiment although not specifically described relative thereto. That is, all embodiments and/or features of any embodiment can be combined in any way and/or combination, even if not specifically described in that manner. These and other aspects of the present invention are explained in detail below.

BRIEF DESCRIPTION OF THE DRAWINGS

The accompanying drawings, which form a part of the specification, illustrate various embodiments of the present invention. The drawings and description together serve to fully explain embodiments of the present invention.

DETAILED DESCRIPTION

Figures 1A, 1B:
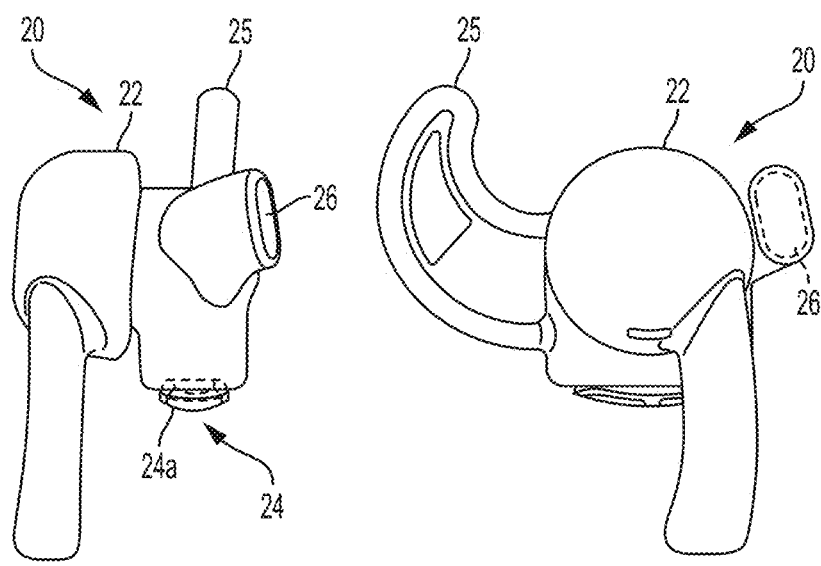
FIGS. 1A-1B illustrate a monitoring device that can be positioned within an ear of a subject, according to some embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment or figure although not specifically described or shown as such.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "secured", "connected", "attached" or "coupled" to another feature or element, it can be directly secured, directly connected, attached or coupled to the other feature or element or intervening features or elements may be present. In contrast, when a feature or element is referred to as being "directly secured", "directly connected", "directly attached" or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the terms "comprise", "comprising", "comprises", "include", "including", "includes", "have", "has", "having", or variants thereof are open-ended, and include one or more stated features, elements, steps, components or functions but does not preclude the presence or addition of one or more other features, elements, steps, components, functions or groups thereof. Furthermore, as used herein, the common abbreviation "e.g.", which derives from the Latin phrase "exempli gratia," may be used to introduce or specify a general example or examples of a previously mentioned item, and is not intended to be limiting of such item. The common abbreviation "i.e.", which derives from the Latin phrase "id est," may be used to specify a particular item from a more general recitation.

As used herein, the term "and/or" includes any and all combinations of one or more of the associated listed items and may be abbreviated as "/".

As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

The term "about", as used herein with respect to a value or number, means that the value or number can vary more or less, for example by +/−20%, +/−10%, +/−5%, +/−1%, +/−0.5%, +/−0.1%, etc.

The terms "sensor", "sensing element", and "sensor module", as used herein, are interchangeable and refer to a sensor element or group of sensor elements that may be utilized to sense information, such as information (e.g., physiological information, body motion, etc.) from the body of a subject and/or environmental information in a vicinity of the subject. A sensor/sensing element/sensor module may comprise one or more of the following: a detector element, an emitter element, a processing element, optics, mechanical support, supporting circuitry, and the like. Both a single sensor element and a collection of sensor elements may be considered a sensor, a sensing element, or a sensor module.

The term "optical emitter", as used herein, may include a single optical emitter and/or a plurality of separate optical emitters that are associated with each other.

The term "optical detector", as used herein, may include a single optical detector and/or a plurality of separate optical detectors that are associated with each other.

The term "wearable sensor module", as used herein, refers to a sensor module configured to be worn on or near the body of a subject.

The terms "monitoring device" and "biometric monitoring device", as used herein, are interchangeable and include any type of device, article, or clothing that may be worn by and/or attached to a subject and that includes at least one sensor/sensing element/sensor module. Exemplary monitoring devices may be embodied in an earpiece, a headpiece, a finger clip, a digit (finger or toe) piece, a limb band (such as an arm band or leg band), an ankle band, a wrist band, a nose piece, a sensor patch, eyewear (such as glasses or shades), apparel (such as a shirt, hat, underwear, etc.), a mouthpiece or tooth piece, contact lenses, or the like.

The term "monitoring" refers to the act of measuring, quantifying, qualifying, estimating, sensing, calculating, interpolating, extrapolating, inferring, deducing, or any combination of these actions. More generally, "monitoring" refers to a way of getting information via one or more sensing elements. For example, "blood health monitoring" includes monitoring blood gas levels, blood hydration, and metabolite/electrolyte levels.

The term "headset", as used herein, is intended to include any type of device or earpiece that may be attached to or near the ear (or ears) of a user and may have various configurations, without limitation. Headsets incorporating optical sensor modules, as described herein, may include mono headsets (a device having only one earbud, one earpiece, etc.) and stereo headsets (a device having two earbuds, two earpieces, etc.), earbuds, hearing aids, ear jewelry, face masks, headbands, and the like. In some embodiments, the term "headset" may include broadly headset elements that are not located on the head but are associated with the headset. For example, in a "medallion" style wireless headset, where the medallion comprises the wireless electronics and the headphones are plugged into or hard-wired into the medallion, the wearable medallion would be considered part of the headset as a whole. Similarly, in some cases, if a mobile phone or other mobile device is intimately associated with a plugged-in headphone, then the term "headset" may refer to the headphone-mobile device combination. The terms "headset" and "earphone", as used herein, are interchangeable.

The term "physiological" refers to matter or energy of or from the body of a creature (e.g., humans, animals, etc.). In embodiments of the present invention, the term "physiological" is intended to be used broadly, covering both physical and psychological matter and energy of or from the body of a creature.

The term "body" refers to the body of a subject (human or animal) that may wear a monitoring device, according to embodiments of the present invention. The term "bodily location" refers to a location of the body on which (or in which) a monitoring device may be worn.

The term "processor" is used broadly to refer to a signal processor or computing system or processing or computing method which may be localized or distributed. For example, a localized signal processor may comprise one or more signal processors or processing methods localized to a general location, such as to a wearable device. Examples of such wearable devices may comprise an earpiece, a headpiece, a finger clip, a digit (finger or toe) piece, a limb band (such as an arm band or leg band), an ankle band, a wrist band, a nose piece, a sensor patch, eyewear (such as glasses or shades), apparel (such as a shirt, hat, underwear, etc.), a mouthpiece or tooth piece, contact lenses, or the like. Examples of a distributed processor comprise "the cloud", the internet, a remote database, a remote processor computer, a plurality of remote processors or computers in communication with each other, or the like, or processing methods distributed amongst one or more of these elements. The key difference is that a distributed processor may include delocalized elements, whereas a localized processor may work independently of a distributed processing system. As a specific example, microprocessors, microcontrollers, ASICs (application specific integrated circuits), analog processing circuitry, or digital signal processors are a few non-limiting examples of physical signal processors that may be found in wearable devices.

The term "remote" does not necessarily mean that a remote device is a wireless device or that it is a long distance away from a device in communication therewith. Rather, the term "remote" is intended to reference a device or system that is distinct from another device or system or that is not substantially reliant on another device or system for core functionality. For example, a computer wired to a wearable device may be considered a remote device, as the two devices are distinct and/or not substantially reliant on each other for core functionality. However, any wireless device (such as a portable device, for example) or system (such as a remote database for example) is considered remote to any other wireless device or system.

The terms "signal analysis frequency" and "signal sampling rate", as used herein, are interchangeable and refer to the number of samples per second (or per other unit) taken from a continuous sensor (i.e., physiological sensor and environmental sensor) signal to ultimately make a discrete signal.

The term "sensor module interrogation power", as used herein, refers to the amount of electrical power required to operate one or more sensors (i.e., physiological sensors and environmental sensors) of a sensor module and/or any processing electronics or circuitry (such as microprocessors and/or analog processing circuitry) associated therewith. Examples of decreasing the sensor interrogation power may include lowering the voltage or current through a sensor element (such as lowering the voltage or current applied to a pair of electrodes), lowering the polling (or polling rate) of a sensor element (such as lowering the frequency at which an optical emitter is flashed on/off in a PPG sensor), lowering the sampling frequency of a stream of data (such as lowering the sampling frequency of the output of an optical detector in a PPG sensor), selecting a lower-power algorithm (such as selecting a power-efficient time-domain processing method for measuring heart rate vs. a more power-hungry frequency-domain processing method), or the like. Lowering the interrogation power may also include powering only one electrode, or powering fewer electrodes, in a sensor module or sensor element such that less total interrogation power is exposed to the body of a subject. For example, lowering the interrogation power of a PPG sensor may comprise illuminating only one light-emitting diode rather than a plurality of light-emitting diodes that may be present in the sensor module, and lowering the interrogation power of a bioimpedance sensor may comprise powering only one electrode pair rather than a plurality of electrodes that may be present in the bioimpedance sensor module.

The term "polling" typically refers to controlling the intensity of an energy emitter of a sensor or to the "polling rate" and/or duty cycle of an energy emitter element in a sensor, such as an optical emitter in a PPG sensor or an ultrasonic driver in an ultrasonic sensor. Polling may also refer to the process of collecting and not collecting sensor data at certain periods of time. For example, a PPG sensor may be "polled" by controlling the intensity of one or more optical emitters, i.e. by pulsing the optical emitter over time. Similarly, the detector of a PPG sensor may be polled by reading data from that sensor only at a certain point in time or at certain intervals, i.e., as in collecting data from the detector of a PPG sensor for a brief period during each optical emitter pulse. A sensor may also be polled by turning on or off one or more elements of that sensor in time, such as when a PPG sensor is polled to alternate between multiple LED wavelengths over time or when an ultrasonic sensor is polled to alternate between mechanical vibration frequencies over time.

The terms "sampling frequency", "signal analysis frequency", and "signal sampling rate", as used herein, are interchangeable and refer to the number of samples per second (or per other unit) taken from a continuous sensor or sensing element (for example, the sampling rate of the thermopile output in a tympanic temperature sensor).

The term "noise reference" refers to a reference information source for an undesired, dynamic noise signal that may be present within a sensor signal. A noise reference signal may be generated by a noise reference source, and this noise reference signal may be processed (i.e., via digital and/or analog electronic processing) to attenuate noise from the sensor signal, yielding a filtered signal that contains cleaner sensor information (i.e., such that the desired sensor information remains with reduced noise). As a specific example, for a PPG sensor worn by a subject, a motion noise reference may include an accelerometer, a pressure sensor, a piezoelectric sensor, a capacitive sensor, an inductive sensor, an optical sensor, or the like. Ideally, the noise reference signal may contain information associated with the motion of the subject, but may contain little (if any) information associated with the blood flow of the subject. Stated another way, the ratio of body motion information to arterial blood flow information contained in the noise reference signal may be relatively high.

Motion noise information generated by the motion noise reference can be processed with PPG sensor data to attenuate dynamically changing motion noise from the PPG sensor, such that the resulting signal contains cleaner information about blood flow (and less motion noise information). In accordance with some embodiments described herein, one motion noise reference for a wearable PPG sensor is an optomechanical sensor also known as a "blocked channel" sensor. This optomechanical sensor can be designed or configured to modulate light generated by an optical emitter in response to body motion, and to direct that light upon a pathway that does not interact with blood flow; in this manner, the optomechanical sensor can be configured to measure body motion and not blood flow motion, so that the noise reference signal may be used to filter out motion noise from the PPG signal with analog or digital signal processing (i.e. filtering). Nonlimiting examples of such noise references are presented in commonly-owned U.S. Pat. No. 9,289,175 entitled "LIGHT-GUIDING DEVICES AND MONITORING DEVICES INCORPORATING SAME," and International Patent Application No. PCT/US2016/046273 entitled "METHODS AND APPARATUS FOR DETECTING MOTION VIA OPTOMECHANICS," the disclosures of which are incorporated by reference herein.

It should be noted that "algorithm" and "circuit" are referred to herein. An algorithm refers to an instruction set, such as an instruction set with sequential steps and logic, that may be in memory whereas a circuit refers to electronic components and/or traces that may implement such logic operations.

It should be noted that processes for managing hysteresis are implied herein. Namely, several embodiments herein for controlling sensors (and other wearable hardware) may involve a processor sending commands to a sensor element depending on the sensor readings. Thus, in some embodiments, a sensor reading (such as a reading from an optical detector or a sensing electrode) above X may result in a processor sending a command to electrically bias another sensor element (such as an optical emitter or a biasing electrode) above Y. Similarly, as soon as the sensor reading drops below X, a processor may send a command to bias another sensor element below Y. However, in borderline situations this may cause unwanted hysteresis in the biasing command, as sensor readings may rapidly toggle above/below X resulting in the toggling of the biasing of another sensor element above/below Y. As such, hysteresis management may be integrated within the algorithm(s) for controlling the execution of a processor. For example, the processor may be configured by the algorithm to delay a biasing command by a period of time Z following the timing of a prior biasing command, thereby preventing or reducing the aforementioned toggling.

In the following figures, various monitoring devices will be illustrated and described for attachment to the ear or an appendage of the human body. However, it is to be understood that embodiments of the present invention are not limited to those worn by humans.

The ear is an ideal location for wearable health and environmental monitors. The ear is a relatively immobile platform that does not obstruct a person's movement or vision. Monitoring devices located at an ear have, for example, access to the inner-ear canal and tympanic membrane (for measuring core body temperature), muscle tissue (for monitoring muscle tension), the pinna, earlobe, and elsewhere (for monitoring blood gas levels), the region behind the ear (for measuring skin temperature and galvanic skin response), and the internal carotid artery (for measuring cardiopulmonary functioning), etc. Virtually all areas of the ear support enough blood perfusion to enable an assessment of blood flow and blood-flow-derived metrics (such as breathing rate, heart rate, blood pressure, RR-interval, and the like) via photoplethysmography (PPG). A particularly good location for PPG may be the region covering the anti-tragus and concha regions of the ear, as the region has high perfusion, is more resistant to motion artifacts, and is in a region away from the ear canal. The ear is also at or near the point of exposure to: environmental breathable toxicants of interest (volatile organic compounds, pollution, etc.); noise pollution experienced by the ear; and lighting conditions for the eye. Furthermore, as the ear canal is naturally designed for transmitting acoustical energy, the ear provides a good location for monitoring internal sounds, such as heartbeat, breathing rate, and mouth motion.

Optical coupling into the blood vessels of the ear may vary between individuals. As used herein, the term "coupling" refers to the interaction or communication between excitation energy (such as light) entering a region and the region itself. For example, one form of optical coupling may be the interaction between excitation light generated from within an optical sensor of a wearable device—such as a wristband, armband, legband, skin-worn patch, neckband, ring, earbud, other device positioned at or within an ear, a headband, or the like—and the blood vessels. In one embodiment, this interaction may involve excitation light entering the skin and scattering from a blood vessel such that the temporal change in intensity of scattered light is proportional to a temporal change in blood flow within the blood vessel. Another form of optical coupling may be the interaction between excitation light generated by an optical emitter within a wearable device and a light-guiding region of the wearable device. Thus, a wearable device with integrated light-guiding capabilities, wherein light can be guided to multiple and/or select regions along the wearable device, can assure that each individual wearing the device will generate an optical signal related to blood flow through the blood vessels. Optical coupling of light to a particular skin region of one person may not yield photoplethysmographic signals for each person. Therefore, coupling light to multiple regions may assure that at least one blood-vessel-rich region will be interrogated for each person wearing the device. Coupling multiple regions of the body to light may also be accomplished by diffusing light from a light source in the device.

According to some embodiments of the present invention, "smart" monitoring devices including, but not limited to, wrist-worn devices, armbands, earbuds, and the like, are provided that can modify biometric signal extraction algorithms based upon a recognition of an activity level of a subject.

FIGS. 1A-1B illustrate a monitoring apparatus 20 configured to be positioned within an ear of a subject, according to some embodiments of the present invention. The illustrated apparatus 20 includes an earpiece body or housing 22, a sensor module 24, a stabilizer 25, and a sound port 26. When positioned within the ear of a subject, the sensor module 24 has a region 24a configured to contact a selected area of the ear. The illustrated sensor region 24a is contoured (i.e., is "form-fitted") to matingly engage a portion of the ear between the anti tragus and acoustic meatus, and the stabilizer is configured to engage the anti-helix. However, monitoring devices in accordance with embodiments of the present invention can have sensor modules with one or more regions configured to engage various portions of the ear. Various types of device configured to be worn at or near the ear may be utilized in conjunction with embodiments of the present invention.

Figure 2A:
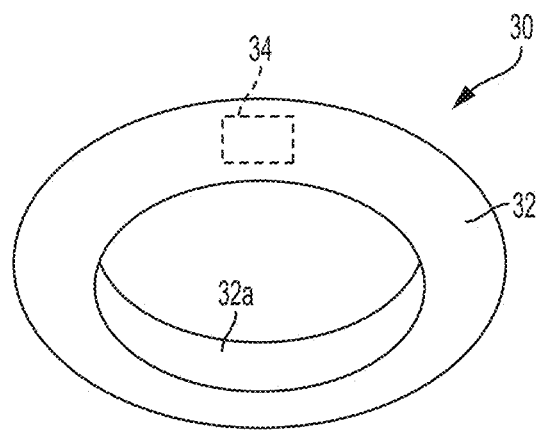
FIG. 2A illustrates a monitoring device that can be positioned around an appendage (such as an arm, leg, finger, toe, etc.) of the body of a subject, according to some embodiments of the present invention.
Figure 2B:
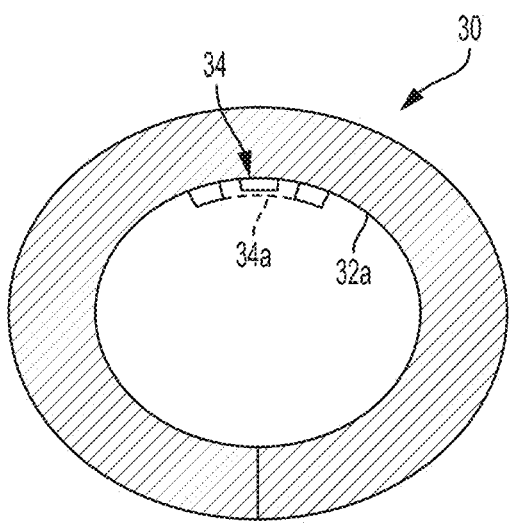
FIG. 2B is a cross sectional view of the monitoring device of FIG. 2A.

FIGS. 2A-2B illustrate a monitoring apparatus 30 in the form of a sensor band 32 configured to be secured to an appendage (e.g., an arm, wrist, hand, finger, toe, leg, foot, neck, etc.) of a subject. The band 32 includes a sensor module 34 on or extending from the inside surface 32a of the band 32. The sensor module 34 is configured to detect and/or measure physiological information from the subject and includes a sensor region 34a that is contoured to contact the skin of a subject wearing the apparatus 30.

Embodiments of the present invention may be utilized in various devices and articles including, but not limited to, patches, clothing, etc. Embodiments of the present invention can be utilized wherever PPG and blood flow signals can be obtained and at any location on the body of a subject. Embodiments of the present invention are not limited to the illustrated monitoring devices 20, 30 of FIGS. 1A-1B and 2A-2B.

The sensor modules 24, 34 for the illustrated monitoring devices 20, 30 of FIGS. 1A-1B and 2A-2B are configured to detect and/or measure physiological information from a subject wearing the monitoring devices 20, 30. In some embodiments, the sensor modules 24, 34 may be configured to detect and/or measure one or more environmental conditions in a vicinity of the subject wearing the monitoring devices 20, 30.

A sensor module utilized in accordance with embodiments of the present invention may be an optical sensor module that includes at least one optical emitter and at least one optical detector. Exemplary optical emitters include, but are not limited to light-emitting diodes (LEDs), laser diodes (LDs), compact incandescent bulbs, micro-plasma emitters, IR blackbody sources, or the like. In addition, a sensor module may include various types of sensors including and/or in addition to optical sensors. For example, a sensor module may include one or more inertial sensors (e.g., an accelerometer, piezoelectric sensor, vibration sensor, photo-reflector sensor, etc.) for detecting changes in motion, one or more thermal sensors (e.g., a thermopile, thermistor, resistor, etc.) for measuring temperature of a part of the body, one or more electrical sensors for measuring changes in electrical conduction, one or more skin humidity sensors, and/or one or more acoustical sensors. Sensor modules may include physiological sensors for monitoring vital signs, blood flow properties, body fluids, muscle motion, body motion, and the like. Sensor modules may include environmental sensors for monitoring ambient light, ambient temperature, ambient humidity, airborne pollutants, wind, and the like. It should be understood that a wide variety of sensors may be incorporated into a wearable sensor module.

Figure 3:
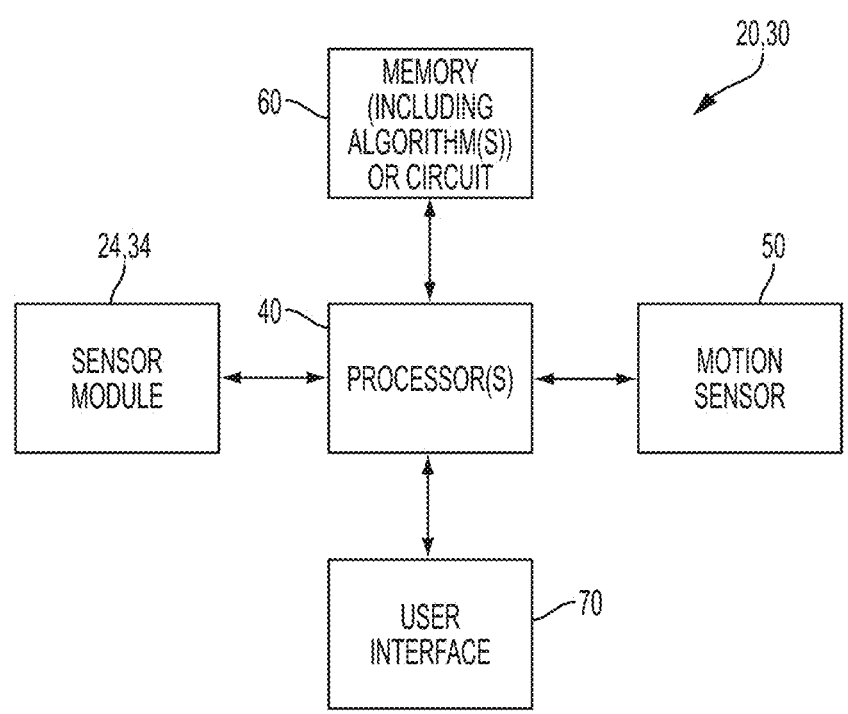
FIG. 3 is a block diagram of a monitoring device according to some embodiments of the present invention.

Referring to FIG. 3, a monitoring device (e.g., monitoring devices 20, 30), according to embodiments of the present invention, is illustrated schematically. The illustrated monitoring device includes a sensor module 24, 34 having one or more physiological sensors configured to detect and/or measure physiological information from the subject, and a motion sensor 50 (e.g., an accelerometer) configured to detect and/or measure subject motion information. The monitoring device 20, 30 also includes at least one processor 40 that is coupled to the sensor(s) of a sensor module 24, 34, to the motion sensor 50, and that is configured to receive and analyze signals produced by the sensor(s) and motion sensor 50.

According to some embodiments of the present invention, the processor 40 is configured to process motion sensor signals to identify an activity characteristic (e.g., periodic or non-periodic activity) of the subject, select or modify a biometric signal extraction algorithm (implemented by computer-readable memory and/or circuit 60) in response to identification of the type of subject activity, and then process physiological sensor signals via the modified biometric signal extraction algorithm or circuit 60 to produce physiological information about the subject, such as subject heart rate, subject respiration rate, subject RRi (i.e., the time-difference between consecutive R-peaks in the ECG or PPG waveform), subject HRV, subject blood pressure, subject blood analyte levels, subject cardiovascular properties, and the like. Although many aspects of this invention are most related to PPG sensors, a variety of other physiological sensors may be used within the scope of this invention.

In some embodiments, the motion sensor 50 is an accelerometer and a filter is applied to each axis of the accelerometer data to remove the DC component therefrom. A spectral transform is performed on each axis of the DC-removed signal over a given time span. An accelerometer spectrum is then generated by taking the root of the sum of the squares of each axis of the accelerometer that is associated with that time span. Other techniques may also be used.

The 1st, 2nd, and 3rd, most intense frequencies and magnitudes in the accelerometer spectrum are identified. The relative proportion of energy within the peaks is compared to all other frequencies to determine if the criteria for periodicity is met. If so, the given segment of time is determined to represent periodic activity and an Automatic Mode Switching feature of the monitoring device is set to inform an algorithm 60 (e.g., a heart rate algorithm, etc.) of the periodic context. If not, an Automatic Mode Switching feature of the monitoring device is set to inform the HR algorithm of the non-periodic context.

Alternatively or in addition, a determination is made whether the ratio of peak frequencies fit a pattern associated with periodicity (e.g., whether peak 2 is twice the frequency of peak 1, etc.). If so, the given segment of time is determined to represent periodic activity and an Automatic Mode Switching feature of the monitoring device is set to inform an algorithm 60 (e.g., a heart rate algorithm, etc.) of the periodic context. If not, an Automatic Mode Switching feature is set to inform the HR algorithm of the non-periodic context.

Figure 4:
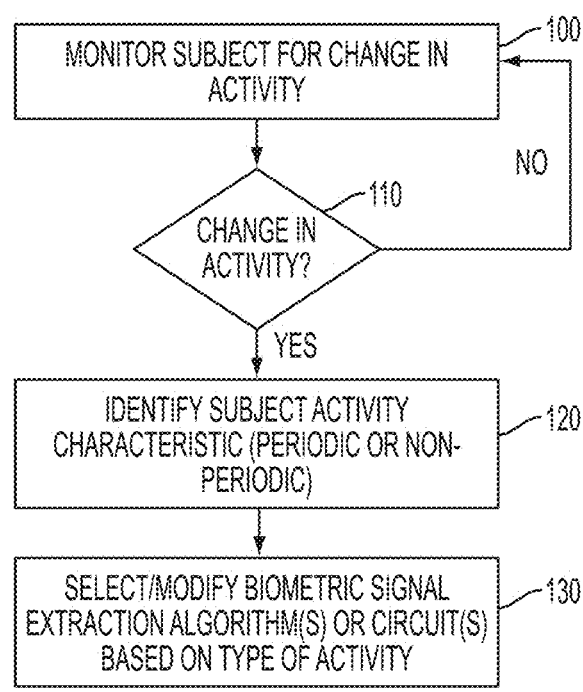
FIGS. 4-7 are flowcharts of operations for monitoring a subject according to embodiments of the present invention.

Referring now to FIG. 4, a method of monitoring a subject via a monitoring device, such as monitoring devices 20, 30, according to some embodiments of the present invention, will be described. The monitoring device includes a physiological sensor configured to detect and/or measure physiological information from the subject and a motion sensor. The physiological sensor and the motion sensor are in communication with a processor that is configured to receive and analyze signals produced by the physiological sensor and motion sensor. The processor may be part of the monitoring device or may be a remotely located processor.

The subject is monitored for a change in physical activity level or type (Block 100). If a change is detected (Block 110), the processor 40 identifies an activity characteristic (e.g., determines if the activity is periodic or non-periodic) (Block 120). For example, via an algorithm stored in or implemented by memory or circuit 60, the processor determines if the subject is engaged in a non-periodic or lifestyle activity such as reading a book, desk work, eating, etc., or a periodic activity such as exercising, running, walking, etc. In response to determining the type of activity, the processing of the biometric signal extraction algorithm may be modified in one or more ways (Block 130). For example, in response to determining the type of activity, at least one parameter of the biometric signal extraction algorithm may be modified, and this modified biometric signal extraction algorithm may be selected for processing. Some specific examples of parameters that may be modified are described in US 2015/0366509 entitled "CADENCE DETECTION BASED ON INERTIAL HARMONICS" (published Dec. 24, 2015), US 2016/0029964 entitled "PHYSIOLOLOGICAL MONITORING DEVICES WITH ADJUSTABLE SIGNAL ANALYSIS AND INTERROGATION POWER AND MONITORING METHODS USING THE SAME" (published Feb. 4, 2016), and US 2015/0011898 entitled "PHYSIOLOGICAL METRIC ESTIMATION RISE AND FALL LIMITING" (published Jan. 8, 2015), the disclosures of which are incorporated by reference herein. For example, parameters affecting the rise or fall time of biometric tracking (such as the tracking of heart rate, breathing rate, RRi, etc.), parameters affecting the subtraction or redaction of unwanted frequencies in the PPG signal (i.e., which frequency bands to subtract or redact (set to zero) based for example on amplitude and/or power), and/or parameters affecting which types of filters to execute (highpass, lowpass, bandpass, active, subtractive or redactive filters, or the like) may be modified. In response to determining the type of activity, the processor may thus select a biometric signal extraction algorithm (which may be all or part of algorithm stored in or implemented by memory or circuit 60) so as to be best suited for processing sensor data during such activity (Block 130) (i.e., that is best suited for removing motion or environmental noise from that particular activity).

It should be noted that, in addition to or alternatively than modifying an algorithm or selecting an algorithm, a circuit may be modified or selected. For example, the determination of periodicity in Block 120 may send a signal to one or more transistors (Block 130) to switch the analog filtering circuits to "notch out" the periodic signal; or, the determination of non-periodicity in Block 120 may send a signal to one or more transistors (Block 130) to switch the analog filtering circuits to a bandpass filter that includes the biometric signals of interest. It should also be noted that both algorithms and circuits may simultaneously be modified or selected in the embodiments described herein. Thus, as another exemplary embodiment, the determination of periodicity in Block 120, using a low-power time-domain algorithm (such as an autocorrelation function, or the like), may initiate an algorithm in Block 130 that determines which frequencies should be removed. The output of the algorithm (i.e., the output from a processor) may send a signal to a bank of analog filters in Block 130 to remove these frequencies without the need for digital removal. This may be advantageous because executing a spectral transform may be overly power-hungry in a wearable device. Physiological sensor signals are then processed via the selected biometric signal extraction algorithm to produce physiological information about the subject, such as subject heart rate, subject respiration rate, subject RRi, subject HRV, subject blood pressure, subject blood analyte levels, subject cardiovascular properties, and the like.

Identification of an activity characteristic (e.g., determining if the activity is periodic or non-periodic) may also be associated with particular metrics to be assessed. For example, detecting that periodic motion exists may be a criteria for determining that a cardiac efficiency metric is being assessed. In contrast, if the subject's motion is aperiodic, then a cardiac efficiency score (Average Cadence/Average HR) may be meaningless. Also, one or more processors or functions may be deactivated or run in power-saving mode based on the detection of type of motion (e.g., a pedometer may be deactivated responsive to detection of aperiodic motion). Additionally, an energy expenditure calculation which factors both HR and footsteps into an equation for the estimation of calories burned may be tuned to detect "fidgeting" (subtle motions) rather than footsteps and update the energy expenditure model to incorporate fidgets and HR, rather than footsteps and HR. The weighting factors for fidgets and HR, for example, may be different than the weighting factors for footsteps and HR when estimating energy expenditure.

Figure 5:
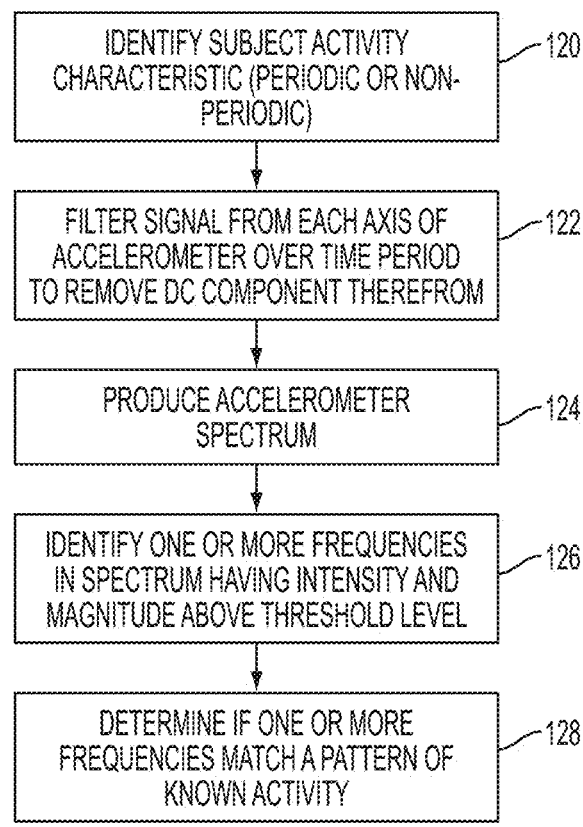

As illustrated in FIG. 5, identifying an activity characteristic of a subject (Block 120) may include filtering a signal from each axis of the accelerometer over a given time period to remove a DC component therefrom (Block 122), producing an accelerometer spectrum using the filtered signals (Block 124), identifying one or more frequencies in the spectrum having a magnitude above a threshold level (Block 126), and/or determining if the one or more frequencies in the spectrum match a pattern associated with a known subject activity mode (Block 128). It should be noted that the operations of FIG. 5 may be controlled by algorithms, circuitry, or a combination of both.

Figure 6:
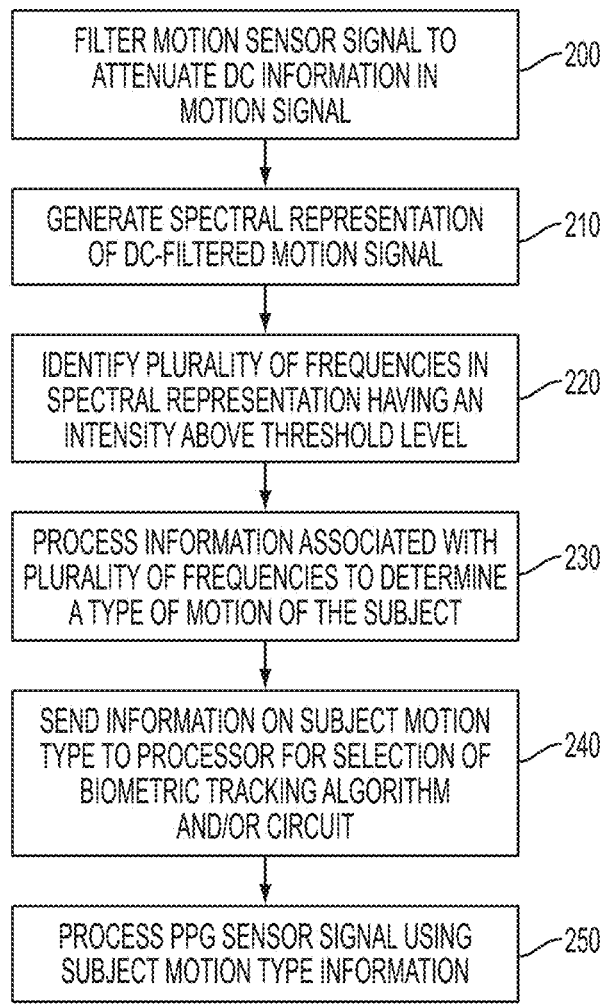

Referring now to FIG. 6, a method of monitoring a subject via a monitoring device, such as monitoring devices 20, 30, according to some embodiments of the present invention, will be described. The monitoring device includes a PPG sensor and a motion sensor which are in communication with a processor that is configured to receive and analyze signals produced by the sensor module and motion sensor. The processor may be part of the monitoring device or may be a remotely located processor. It should be noted that the operations of FIG. 6 may be controlled by algorithms, circuitry, or a combination of both.

The method includes filtering a motion signal generated by the motion sensor to attenuate DC information in the motion signal and generate a DC-filtered motion signal (Block 200). A spectral representation of the DC-filtered motion signal is generated (Block 210) and a plurality of frequencies in the spectral representation are identified having a magnitude above a threshold level (Block 220). In other words, the most intense frequencies in the spectral representation are identified. Additional operations may include filtering a step rate component from a measured heart rate component based on a function of a difference therebetween as described in US 2015/0018636 entitled "REDUCTION OF PHYSIOLOGICAL METRIC ERROR DUE TO INERTIAL CADENCE" (published Jan. 15, 2015), comparing frequency measurements from an inertial sensor with one or more thresholds as described in US 2015/0366509 entitled "CADENCE DETECTION BASED ON INERTIAL HARMONICS" (published Dec. 24, 2015), and measuring signal quality to determine how a user should adjust a monitoring device to improve biometric fit, as described in US 2016/0094899 entitled "METHODS AND APPARATUS FOR IMPROVING SIGNAL QUALITY IN WEARABLE BIOMETRIC MONITORING DEVICES" (published Mar. 31, 2016), individually or together in combination, the disclosures of which are incorporated by reference herein. Information associated with the plurality of frequencies is then processed to determine a type of motion of the subject, for example, whether the subject motion is periodic or non-periodic motion (Block 230). Information on the subject motion type is sent to a biometric tracking algorithm or circuit or is otherwise used by the processor to select a biometric tracking algorithm or circuit (Block 240), and a PPG sensor signal is processed using the biometric tracking algorithm or circuit corresponding to the subject motion type information to generate biometric information about the subject (Block 250). Exemplary biometric information includes, but is not limited to, subject heart rate, subject respiration rate, subject RRi, subject HRV, subject blood pressure, subject blood analyte levels, subject cardiovascular properties, etc.

Figure 7:
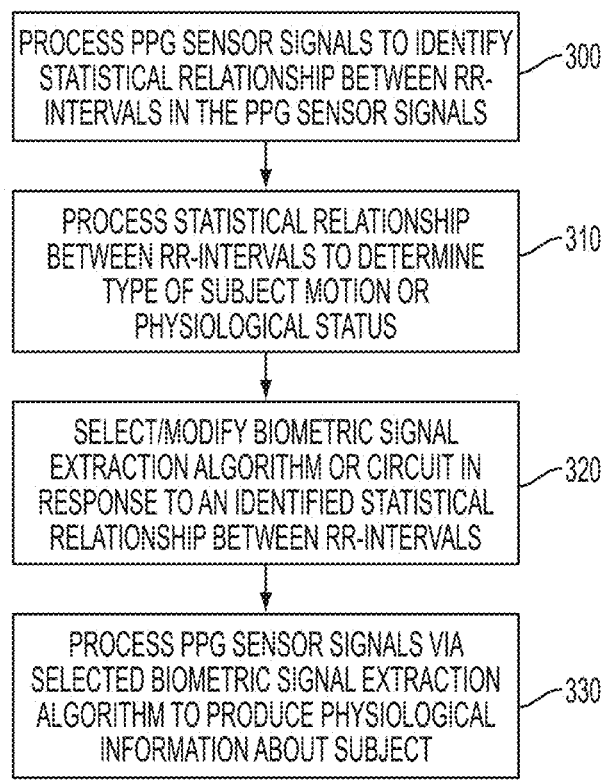

Referring now to FIG. 7, a method of monitoring a subject via a monitoring device, such as monitoring devices 20, 30, according to some embodiments of the present invention, will be described. The monitoring device includes a PPG sensor and a motion sensor which are in communication with a processor that is configured to receive and analyze signals produced by the sensor module and motion sensor. The processor may be part of the monitoring device or may be a remotely located processor. It should be noted that the operations of FIG. 7 may be controlled by algorithms, circuitry, or a combination of both.

The method includes processing PPG sensor signals via the at least one processor to identify a statistical relationship between RR-intervals in the PPG sensor signals (Block 300) and processing the statistical relationship between RR-intervals to determine a type of motion of the subject (e.g., periodic or non-periodic) or a physiological status of the subject (Block 310). A biometric signal extraction algorithm or circuit is modified or selected via the processor in response to an identified statistical relationship between RR-intervals (Block 320). PPG sensor signals are then processed via the selected biometric signal extraction algorithm to produce physiological information about the subject (Block 320), such as subject heart rate, subject respiration rate, subject RR-interval (RRi), subject HRV, subject blood pressure, subject blood analyte levels, subject cardiovascular properties, etc. A particular example of processing RR-intervals to determine a type of motion of the subject may include processing a series of RR-intervals to identify the existence of stress, which may be associated with aperiodic (non-periodic) motion.

It should be noted that it is known to those skilled in the art that a series of RR-intervals may be processed to generate an assessment of fatigue, stress (particularly psychosocial stress), autonomic nervous functioning, hemodynamics, cardiac disease—such as atrial fibrillation or cardiac arrhythmia—or the like. However, the inventors have discovered that the statistical analysis alone may not be sufficient to generate sufficient physiological information for a diagnosis of a health condition or other physiological state. Thus, in one particular embodiment of FIG. 7, the RRi-intervals may be statistically processed (Block 310) to generate an assessment that a subject status of atrial fibrillation is likely. Once this status is known to be likely, the signal extraction algorithm may be modified or selected to more concretely determine a status of atrial fibrillation or to diagnose another condition (such as poor or abnormal hemodynamics or cardiac output, which may be associated with atrial fibrillation). As a specific example, Block 320 may switch to an algorithm that allows more frequencies to pass through during signal extraction, such that the extracted signal from Block 320 may be further processed by Block 330 to generate sufficient physiological information to diagnose atrial fibrillation. It should be understood that this describes a particular embodiment, and other embodiments that rely on FIG. 7 may be used with the present invention. As another specific example, Block 310 may determine that a subject may likely be in a status of fatigue. Block 320 may then modify or select a signal extraction algorithm that increases the signal resolution (i.e., the sampling rate and/or dynamic range), such that the extracted signal may be processed by Block 330 to generate a more definitive assessment of fatigue. In yet another example, Block 310 may determine that a subject may likely be in a status of stress, Block 320 may then modify or select a signal extraction algorithm that switches from a screening spectral-based (frequency domain-based) RRi calculator to a higher resolution time-domain-based RRi calculator, the extracted RRi signal may then be processed by Block 330 to generate a more definitive assessment of stress.

Figure 8:
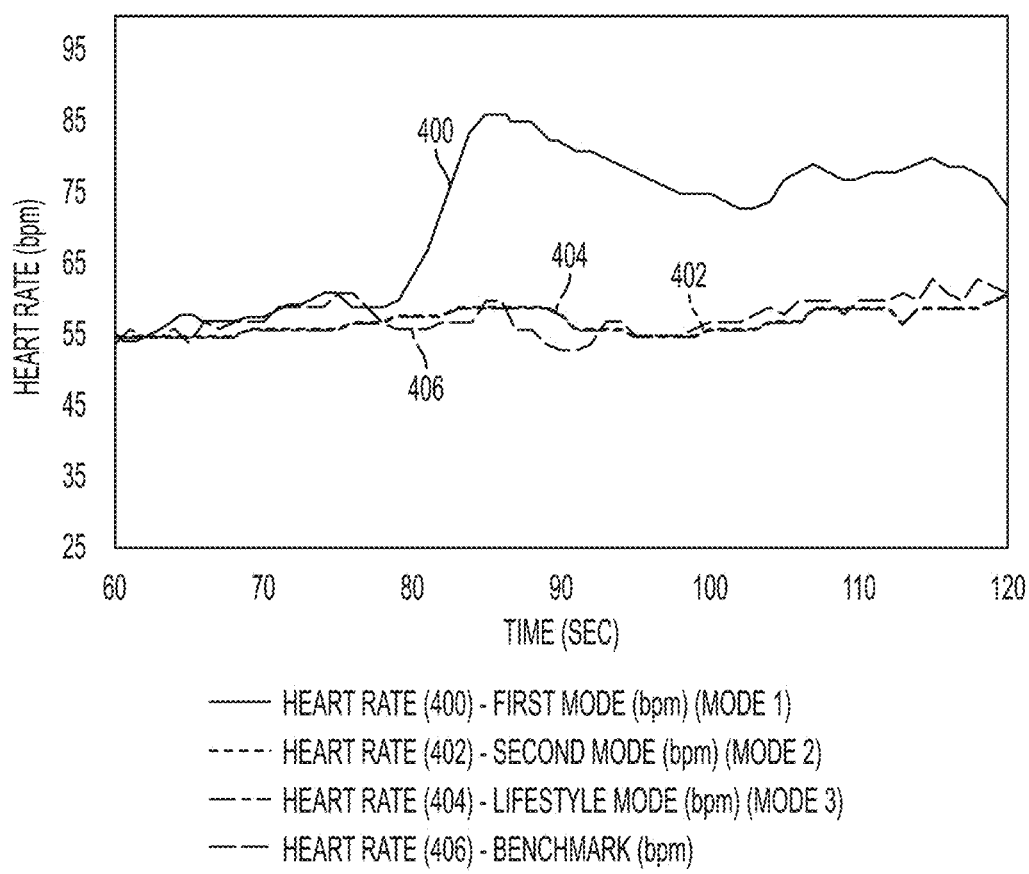
FIG. 8 is a graph illustrating heart rate data for a subject plotted over time compared to a benchmark for a range of activity mode settings of a monitoring device, according to some embodiments of the present invention.

FIG. 8 is a graph illustrating heart rate data 400, 402, 404 for a subject plotted over time compared to the actual heart rate (406), the heart rate determined by a validated benchmark device, for a range of activity mode settings for a monitoring device according to some embodiments of the present invention. For the illustrated duration, the subject was not walking/jogging/running (i.e., the subject was not engaged in a periodic activity), but was doing deskwork (i.e., the subject was engaged in a non-periodic activity), where arms and hands were moving as is typical for desk work. As seen, the heart rate in Mode 3 (the "lifestyle mode" indicated by 404) most closely agrees with that of the benchmark device heart rate (406), and the monitoring device correctly uses the output for Mode 3.

Figure 9:
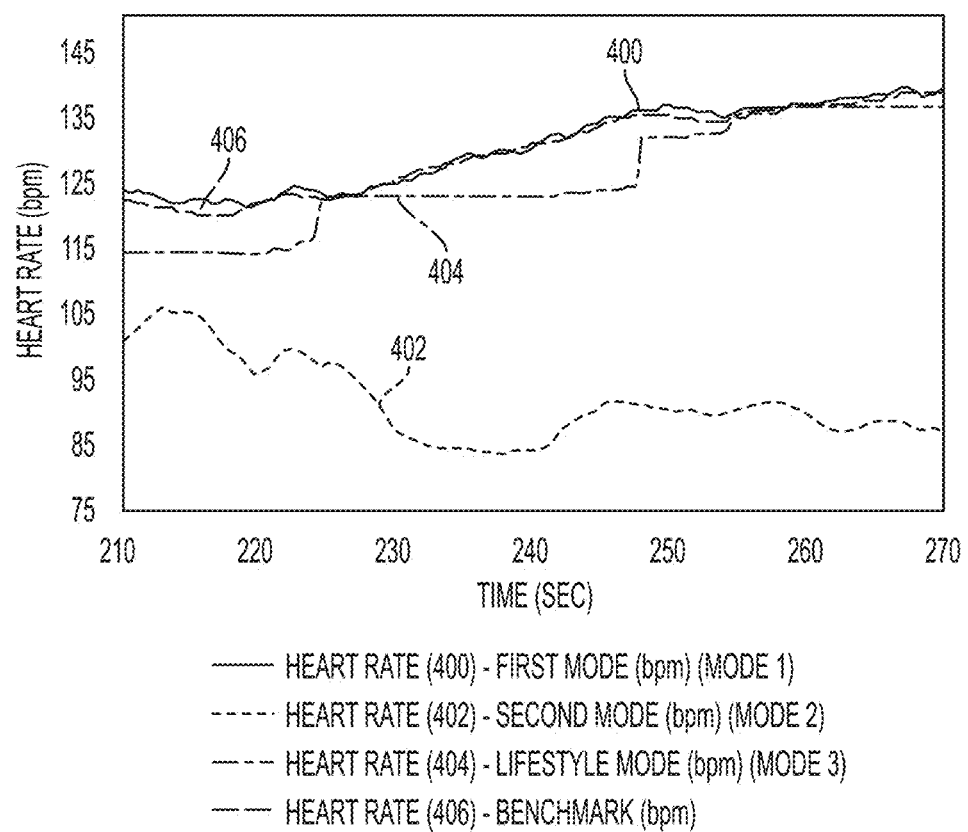
FIG. 9 is a graph illustrating heart rate data for a subject plotted over time compared to a benchmark for a range of activity mode settings of a monitoring device, according to some embodiments of the present invention.

FIG. 9 is a graph illustrating heart rate data 400, 402, 404 for a subject plotted over time compared to the actual heart rate (406), the heart rate determined by a validated benchmark device, for a range of activity mode settings for a monitoring device according to some embodiments of the present invention. For the illustrated duration, the subject is jogging. As seen, the heart rate in Mode 1 (400) most closely agrees with that of the benchmark device heart rate (406), and the monitoring device correctly uses the output for Mode 1. Note that the heart rate reported using Lifestyle mode (404) does not match the benchmark (406) as well as Mode 1 output (400).

Figure 10:
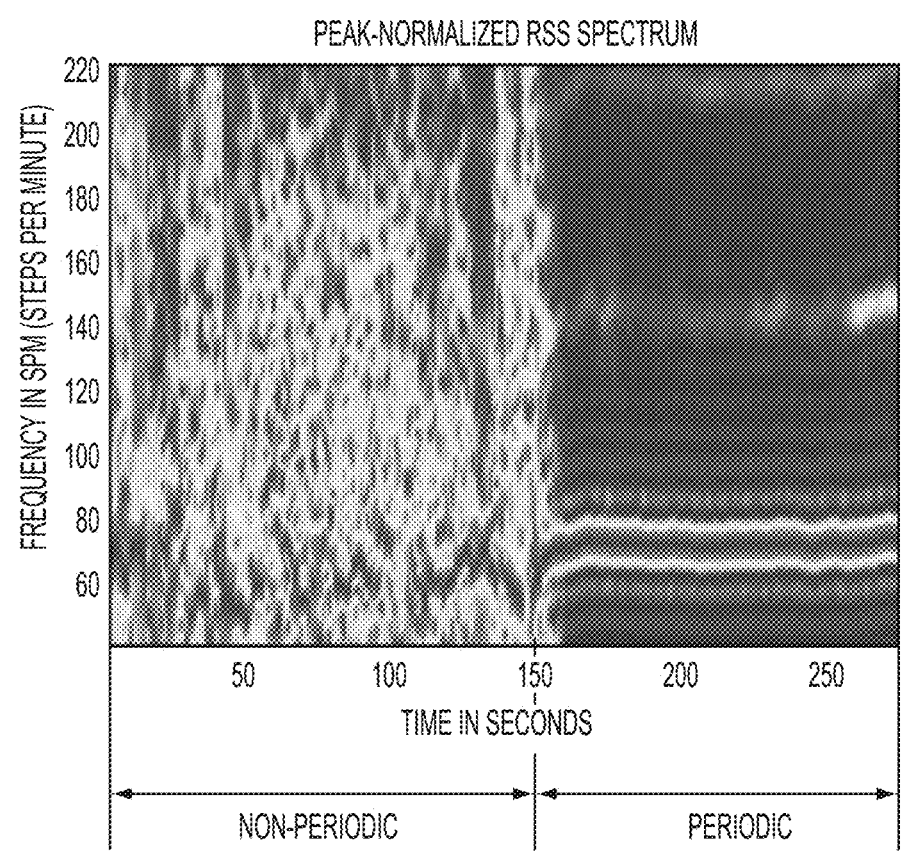
FIG. 10 is a spectrogram of accelerometer data showing the subject monitored in FIGS. 8 and 9 performing non-periodic activity and periodic activity.

FIG. 10 is a spectrogram for exemplary combined accelerometer data showing the subject monitored in FIGS. 8 and 9 performing non-periodic activity from time (t)=0 to 150 seconds, and performing periodic activity (walking) after t=150 seconds. For accurate heart rate tracking, the monitoring device uses settings associated with Lifestyle Mode (Mode 3) prior to t=150 sec and Periodic Mode after t=120 seconds.

Returning to FIG. 4, a method of monitoring a subject via a monitoring device, block 130 may be modified in accordance with additional embodiments based on the detection of periodic or non-periodic motion. For example, in one embodiment shown as Block 144 in FIG. 11, if the processor 40 identifies an activity characteristic (e.g., determines if the activity is periodic or non-periodic) (Block 120) responsive to monitoring a subject (Block 100) and detecting a change in activity (Block 110), then a particular noise reference or set of noise references may be selected for improved (or optimal) motion noise reduction (or removal) from a physiological signal (Block 144). As a specific example for a PPG sensor (such as that similar to that of FIG. 2 and/or FIG. 3) worn by a subject, the PPG sensor having both optical sensors and a plurality of motion sensors, it may be desirable to select a particular type of motion sensor (or a particular set of motion sensors) to remove periodic noise and to select a different type of motion sensor (or a set of different motion sensors) to remove aperiodic noise. For example, upon determining at Block 120 that the activity characteristic is periodic, in Block 144 an accelerometer may be selected as the noise reference. As with descriptions of FIG. 4, this selection may be controlled by one or more algorithms on a microprocessor and/or electronic circuitry. In contrast, upon detecting that the activity characteristic is aperiodic, an optomechanical sensor, such as "blocked channel sensor", may be selected as the noise reference.

One reason why an accelerometer may be a more suitable noise reference for periodic motion over an optomechanical sensor is because an accelerometer may have a better dynamic range or may have a stronger signal response at intense motions associated with periodic motion (such as running, sprinting, cycling, or the like). In contrast, an optomechanical sensor may have a better sensitivity and/or resolution at less intense motion levels (such as resting, walking, typing, grabbing, or the like) or may have a stronger signal response at less intense motions associated with aperiodic motion. Moreover, for a PPG sensor, because the signal response of an optomechanical noise reference may more closely resemble or otherwise correspond to the unwanted motion-related optical noise from the PPG sensor signal, the PPG and optomechanical sensors are likely to be more linear with each other than would be the paring of a PPG sensor and inertial noise reference (such as an accelerometer). Thus, time-domain-based PPG motion noise removal methods or algorithms (such as adaptive filtering and the like), often well-suited for aperiodic motion, may be more effective with this high linearity. In contrast, frequency-domain-based PPG motion noise removal methods or algorithms (such as spectral subtraction and the like), often well-suited for periodic motion, may not be as sensitive to the linearity between the PPG sensor and the noise reference and may work more effectively with an inertial noise reference.

Figure 11:
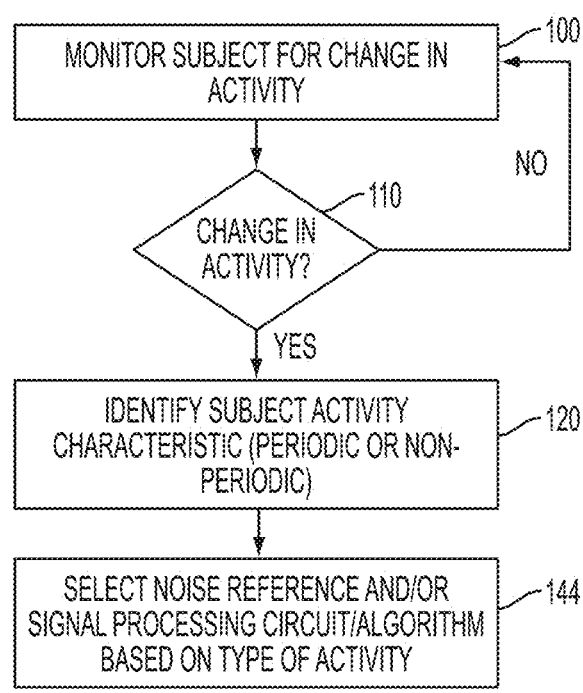
FIG. 11 is a flowchart of operations for selecting a noise reference responsive to monitoring a subject according to embodiments of the present invention.

Considering a pressure sensor as an example of a "motion sensor" in FIG. 4 and FIG. 11, in one embodiment a detection of aperiodic motion may result in an accelerometer being deselected as the noise reference and a pressure sensor being selected as a noise reference (or a combination of a pressure sensor and an accelerometer). This is because (as with an optomechanical sensor) a pressure sensor may be more sensitive to aperiodic motion than an inertial sensor but may also be less effective at sensing periodic motion. In some embodiments, Block 144 may not change the noise reference in response to Block 120 but rather may change the algorithm or circuit for noise reduction or removal using the same noise reference. As a specific example, the detection of periodic motion (Block 120) may trigger a spectral noise (frequency domain) reduction or removal algorithm using an accelerometer as a noise reference (Block 130), but the detection of aperiodic motion may trigger a time-domain noise reduction or removal algorithm using the same accelerometer as a noise reference. This may be beneficial because spectral noise reduction or removal algorithms may be more suited for periodic activities (especially where "cross-overs" between step rate and heart rate are observed) and time-domain noise reduction or removal algorithms may be more suited for aperiodic activities (where "cross-overs" are much less likely).

Example embodiments are described herein with reference to block diagrams and flowchart illustrations. It is understood that a block of the block diagrams and flowchart illustrations, and combinations of blocks in the block diagrams and flowchart illustrations, can be implemented by computer program instructions that are performed by one or more computer circuits. These computer program instructions may be provided to a processor circuit of a general purpose computer circuit, special purpose computer circuit, and/or other programmable data processing circuit to produce a machine, such that the instructions, which execute via the processor of the computer and/or other programmable data processing apparatus, transform and control transistors, values stored in memory locations, and other hardware components within such circuitry to implement the functions/acts specified in the block diagrams and flowchart block or blocks, and thereby create means (functionality) and/or structure for implementing the functions/acts specified in the block diagrams and flowchart blocks.

These computer program instructions may also be stored in a tangible computer-readable medium that can direct a computer or other programmable data processing apparatus to function in a particular manner, such that the instructions stored in the computer-readable medium produce an article of manufacture including instructions which implement the functions/acts specified in the block diagrams and flowchart blocks.

A tangible, non-transitory computer-readable medium may include an electronic, magnetic, optical, electromagnetic, or semiconductor data storage system, apparatus, or device. More specific examples of the computer-readable medium would include the following: a portable computer diskette, a random access memory (RAM) circuit, a read-only memory (ROM) circuit, an erasable programmable read-only memory (EPROM or Flash memory) circuit, a portable compact disc read-only memory (CD-ROM), and a portable digital video disc read-only memory (DVD/Blu-Ray).

The computer program instructions may also be loaded onto a computer and/or other programmable data processing apparatus to cause a series of operational steps to be performed on the computer and/or other programmable apparatus to produce a computer-implemented process such that the instructions which execute on the computer or other programmable apparatus provide steps for implementing the functions/acts specified in the block diagrams and flowchart blocks. Accordingly, embodiments of the present invention may be embodied in hardware and/or in software (including firmware, resident software, micro-code, etc.) that runs on a processor such as a digital signal processor, which may collectively be referred to as "circuitry," "a module" or variants thereof.

It should also be noted that in some alternate implementations, the functions/acts noted in the blocks may occur out of the order noted in the flowcharts. For example, two blocks shown in succession may in fact be executed substantially concurrently or the blocks may sometimes be executed in the reverse order, depending upon the functionality/acts involved. Moreover, the functionality of a given block of the flowcharts and block diagrams may be separated into multiple blocks and/or the functionality of two or more blocks of the flowcharts and block diagrams may be at least partially integrated. Finally, other blocks may be added/inserted between the blocks that are illustrated. Moreover, although some of the diagrams include arrows on communication paths to show a primary direction of communication, it is to be understood that communication may occur in the opposite direction to the depicted arrows.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A method of monitoring a subject via a monitoring device, wherein the monitoring device includes a physiological sensor and a plurality of motion sensors, and wherein the physiological sensor and the plurality of motion sensors are in communication with at least one processor, the method comprising:
   processing, via the at least one processor, a motion sensor signal to identify an activity characteristic of the subject;
   selecting one of the plurality of motion sensors as a noise reference via the at least one processor in response to based on identification of the activity characteristic; and
   processing, via the at least one processor, a physiological sensor signal received from the physiological sensor using the noise reference to generate an output signal having reduced noise relative to the physiological sensor signal.

2. The method of claim 1, wherein the plurality of motion sensors comprises first and second motion sensors, wherein the first and second motion sensors are different types of sensors, and wherein selecting the one of the plurality of motion sensors as the noise reference comprises:
   selecting, from among the first and second motion sensors, the first motion sensor as the noise reference based on identification of the activity characteristic as periodic motion; or
   selecting, from among the first and second motion sensors, the second motion sensor as the noise reference based on identification of the activity characteristic as non-periodic motion.

3. The method of claim 2, wherein the physiological sensor comprises an optical sensor, and wherein the second motion sensor is configured to provide a signal response that more closely corresponds to motion-related optical noise present in the physiological sensor signal than the first motion sensor.

4. The method of claim 2, wherein processing the physiological sensor signal using the noise reference comprises:
   processing the physiological sensor signal using a frequency-domain-based algorithm or circuit responsive to identification of the activity characteristic as periodic motion; or
   processing the physiological sensor signal using a time-domain-based algorithm or circuit responsive to identification of the activity characteristic as non-periodic motion.

5. The method of claim 2, wherein the physiological sensor is a photoplethysmography (PPG) sensor, wherein the first motion sensor comprises an inertial sensor, and wherein the second motion sensor comprises an optomechanical sensor.

6. The method of claim 5, wherein the optomechanical sensor is configured to modulate light generated by an optical emitter in response to body motion, and to direct the light upon a pathway which is substantially unaffected by blood flow.

7. The method of claim 1, wherein processing the physiological sensor signal using the noise reference further comprises:
   in response to identification of the activity characteristic as periodic motion, processing the physiological sensor signal using a first algorithm or circuit; or
   in response to identification of the activity characteristic as non-periodic motion, processing the physiological sensor signal using a second algorithm or circuit that is different from the first algorithm or circuit.

8. The method of claim 7, wherein the first algorithm or circuit comprises frequency-domain processing and/or filtering, and wherein the second algorithm or circuit comprises time-domain processing and/or filtering.

9. The method of claim 8, wherein the first and second algorithms or circuits utilize a same sensor or sensors of the plurality of motion sensors.

10. The method of claim 8, wherein the first algorithm or circuit is configured to perform spectral subtraction, and wherein the second algorithm or circuit is configured to perform adaptive filtering.

11. The method of claim 1, wherein body motion information contained in the noise reference is greater than blood flow information contained therein.

12. The method of claim 1, wherein the noise reference comprises information associated with motion of the subject and is substantially free of information associated with blood flow of the subject.

13. The method of claim 1, wherein the physiological information includes one or more of the following: subject heart rate, subject respiration rate, subject RR-interval (RRi), subject heart rate variability (HRV), subject blood pressure, subject blood analyte levels, subject cardiovascular properties.

14. The method of claim 1, wherein the activity characteristic comprises a first activity characteristic or a second activity characteristic that is different than the first activity characteristic, wherein the plurality of motion sensors comprises first and second motion sensors, wherein the first and second motion sensors are different types of sensors, and wherein selecting the one of the plurality of motion sensors as the noise reference comprises:
  selecting, from among the first and second motion sensors, the first motion sensor as the noise reference based on identification of the first activity characteristic; or
  selecting, from among the first and second motion sensors, the second motion sensor as the noise reference based on identification of the second activity characteristic.

15. The method of claim 14, wherein the first motion sensor comprises an inertial sensor, and wherein the second motion sensor comprises an optomechanical sensor.

16. A monitoring device configured to be attached to a bodily location of a subject, the monitoring device comprising:
  a physiological sensor configured to detect and/or measure physiological data from the subject and generate a physiological sensor signal representative thereof;
  a plurality of motion sensors, each configured to detect and/or measure subject motion data and generate a respective motion sensor signal representative thereof; and
  at least one processor coupled to the physiological sensor and the plurality of motion sensors, wherein the at least one processor is configured to perform operations comprising:
    processing the respective motion sensor signal received from one of the plurality of motion sensors to identify an activity characteristic of the subject;
    selecting one of the plurality of motion sensors as a noise reference based on identification of the activity characteristic; and
    processing the physiological sensor signal received from the physiological sensor using the noise reference to generate an output signal having reduced noise relative to the physiological sensor signal.

17. The monitoring device of claim 16, wherein the plurality of motion sensors comprises first and second motion sensors, wherein the first and second motion sensors are different types of sensors, and wherein selecting the one of the plurality of motion sensors as the noise reference comprises:
  selecting, from among the first and second motion sensors, the first motion sensor as the noise reference based on identification of the activity characteristic as periodic motion; or
  selecting, from among the first and second motion sensors, the second motion sensor as the noise reference based on identification of the activity characteristic as non-periodic motion.

18. The monitoring device of claim 17, wherein the physiological sensor comprises an optical sensor, and wherein a signal response of the second motion sensor more closely corresponds to motion-related optical noise present in the physiological sensor signal than a signal response of the first motion sensor.

19. The monitoring device of claim 18, wherein processing the physiological sensor signal using the noise reference comprises:
  processing the physiological sensor signal using a frequency-domain-based algorithm or circuit responsive to identification of the activity characteristic as periodic motion; or
  processing the physiological sensor signal using a time-domain-based algorithm or circuit responsive to identification of the activity characteristic as non-periodic motion.

20. The monitoring device of claim 19, wherein the physiological sensor is a photoplethysmography (PPG) sensor, wherein the first motion sensor comprises an inertial sensor, and wherein the second motion sensor comprises an optomechanical sensor.

21. The monitoring device of claim 20, wherein the optomechanical sensor is configured to modulate light generated by an optical emitter in response to body motion, and to direct the light upon a pathway which is substantially unaffected by blood flow.

22. A computer program product comprising a non-transitory computer readable storage medium having computer readable program code embodied therein, which, when executed by at least one processor, causes the at least one processor to perform operations comprising:
  processing a motion sensor signal to identify an activity characteristic of the subject;
  selecting one of a plurality of motion sensors as a noise reference based on identification of the activity characteristic; and
  processing a physiological sensor signal received from the physiological sensor using the noise reference to generate an output signal having reduced noise relative to the physiological sensor signal.

* * * * *

UNITED STATES PATENT AND TRADEMARK OFFICE
CERTIFICATE OF CORRECTION

PATENT NO. : 10,945,618 B2
APPLICATION NO. : 15/922610
DATED : March 16, 2021
INVENTOR(S) : Aumer et al.

Page 1 of 1

It is certified that error appears in the above-identified patent and that said Letters Patent is hereby corrected as shown below:

In the Claims

Column 19, Lines 63-64, Claim 1:
Delete "processor in response to based on identification"
Insert -- processor based on identification --

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*